US008603308B2

(12) United States Patent
Bhullar et al.

(10) Patent No.: US 8,603,308 B2
(45) Date of Patent: Dec. 10, 2013

(54) ELECTRICAL PATTERNS FOR BIOSENSOR AND METHOD OF MAKING

(75) Inventors: Raghbir Singh Bhullar, Indianapolis, IN (US); Mike Celenatano, Fishers, IN (US); Said K. El-Rahaiby, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 267 days.

(21) Appl. No.: 12/770,507

(22) Filed: Apr. 29, 2010

(65) Prior Publication Data

US 2011/0000785 A1 Jan. 6, 2011

Related U.S. Application Data

(63) Continuation of application No. PCT/EP2008/009143, filed on Oct. 29, 2008.

(60) Provisional application No. 60/984,279, filed on Oct. 31, 2007.

(51) Int. Cl.
*G01N 27/327* (2006.01)
*C12Q 1/25* (2006.01)
*H05K 3/00* (2006.01)

(52) U.S. Cl.
USPC .............. 204/403.01; 29/825; 29/846; 29/847

(58) Field of Classification Search
USPC ........... 204/403.01–403.15; 29/825, 846, 847
See application file for complete search history.

(56) References Cited

U.S. PATENT DOCUMENTS

| 4,752,455 A | 6/1988 | Mayer |
| 4,895,735 A | 1/1990 | Cook |

(Continued)

FOREIGN PATENT DOCUMENTS

| JP | 62-224002 A | 10/1987 |
| JP | 2002-506205 | 2/2002 |

(Continued)

OTHER PUBLICATIONS

International Preliminary Report on Patentability; PCT/EP2008/009143; May 14, 2010.

(Continued)

*Primary Examiner* — Luan Van
*Assistant Examiner* — Maris R Kessel
(74) *Attorney, Agent, or Firm* — Bose McKinney & Evans LLP

(57) ABSTRACT

The present invention provides an inventive biosensor that includes multiple regions in which the electrical pattern is formed from different electrically conductive materials. The present invention also provides an inventive method for mass producing biosensors as just described. In one embodiment of this method, first and second different electrically conductive materials are deposited side by side on a portion of an electrically insulating base material, and a plurality of electrical patterns is formed on the portion of the base material. Each electrical pattern includes a first region formed from the first electrically conductive material electrically connected to a second region formed from the second electrically conductive material. The electrically conductive materials can be deposited as layers on the base material and portions of the layers can be removed to form the electrical patterns, or, the electrical patterns can be formed by transferring the conductive material in the shape of the electrical pattern directly to the base material, such as by a laser direct transfer technique.

42 Claims, 15 Drawing Sheets

(56) References Cited

U.S. PATENT DOCUMENTS

| | | | |
|---|---|---|---|
| 4,935,345 A | 6/1990 | Guilbeau et al. | |
| 4,970,196 A | 11/1990 | Kim et al. | |
| 4,987,006 A | 1/1991 | Williams et al. | |
| 5,173,441 A | 12/1992 | Yu et al. | |
| 5,292,559 A | 3/1994 | Joyce, Jr. et al. | |
| 5,413,690 A | 5/1995 | Kost et al. | |
| 5,492,861 A | 2/1996 | Opower | |
| 5,512,159 A * | 4/1996 | Yoshioka et al. | 204/403.08 |
| 5,725,914 A | 3/1998 | Opower | |
| 5,729,706 A | 3/1998 | Terane | |
| 5,736,464 A | 4/1998 | Opower | |
| 5,762,770 A | 6/1998 | Pritchard et al. | |
| 5,798,031 A | 8/1998 | Charlton et al. | |
| 6,129,823 A | 10/2000 | Hughes et al. | |
| 6,151,519 A | 11/2000 | Sugihara et al. | |
| 6,177,151 B1 | 1/2001 | Chrisey et al. | |
| 6,212,417 B1 * | 4/2001 | Ikeda et al. | 204/403.14 |
| 6,270,637 B1 | 8/2001 | Crismore et al. | |
| 6,540,890 B1 | 4/2003 | Bhullar et al. | |
| 6,770,180 B1 | 8/2004 | Diehl | |
| 6,822,176 B1 | 11/2004 | Fazzio | |
| 7,073,246 B2 | 7/2006 | Bhullar et al. | |
| 7,101,472 B2 | 9/2006 | Dineen et al. | |
| 2005/0013731 A1 | 1/2005 | Burke et al. | |
| 2005/0016844 A1 | 1/2005 | Burke et al. | |
| 2005/0023137 A1 | 2/2005 | Bhullar et al. | |
| 2005/0103624 A1 | 5/2005 | Bhullar et al. | |
| 2005/0279631 A1 | 12/2005 | Celentano | |
| 2006/0200981 A1 | 9/2006 | Bhullar et al. | |
| 2006/0200982 A1 | 9/2006 | Bhullar et al. | |
| 2007/0017824 A1 * | 1/2007 | Rippeth et al. | 205/792 |

FOREIGN PATENT DOCUMENTS

| | | |
|---|---|---|
| JP | 2003-511851 | 3/2003 |
| JP | 2005/233808 | 9/2005 |
| JP | 2007-524076 A | 8/2007 |
| WO | WO99/45375 A1 | 9/1999 |
| WO | WO01/25775 A1 | 4/2001 |
| WO | WO2004/113902 A1 | 12/2004 |
| WO | WO 2005/066616 A2 | 7/2005 |
| WO | WO 2005/124331 A1 | 12/2005 |
| WO | WO 2007/033079 A3 | 3/2007 |

OTHER PUBLICATIONS

International Search Report and Written Opinion of the International Searching Authority; PCT/EP2008/009143; Feb. 24, 2009.

Schultze, V.; Wagner, M.; "Laser-Induced Forward Transfer of Aluminium," Applied Surface Science 52 (1991) 303-309.

* cited by examiner

ELECTRICAL PATTERNS FOR BIOSENSOR AND METHOD OF MAKING

RELATED APPLICATIONS

This application is a continuation of International Patent Application Number PCT/EP2008/009143 filed on Oct. 29, 2008, which claims the benefit of U.S. Patent Application Ser. No. 60/984,279 filed on Oct. 31, 2007, both of which are incorporated herein by reference in their entireties.

FIELD OF THE INVENTION

The present invention relates generally to the testing of body fluids for concentration of analytes and more particularly to an electrochemical biosensor for such testing and a method of making the same.

BACKGROUND

Test strips or biosensors are often used to measure the presence and/or concentrations of selected analytes in fluid test samples. For example, a variety of test strips are used to measure glucose concentrations in blood to monitor the blood sugar level of people with diabetes. These test strips include a reaction chamber into which a reagent composition has been deposited. Current trends in test strips require smaller test samples and faster analysis times. This provides a significant benefit to the patient, allowing the use of smaller blood samples that can be obtained from less sensitive areas of the body. Additionally, regarding measurement systems for blood glucose, for example, faster test times and more accurate results enable patients to better control their blood sugar level.

Electrochemical biosensors are well known and have been used to determine the concentration of various analytes from biological samples, particularly from blood. Examples of such electrochemical biosensors are described in U.S. Pat. Nos. 5,413,690; 5,762,770; 5,798,031; 6,129,823 and published application US2005/0013731, each of which is hereby incorporated by reference. For example, US2005/0013731 discloses an electrochemical biosensor having a covering layer US2005/0013731 discloses an electrochemical biosensor having a covering layer overlying a base substrate. The base substrate has an electrical pattern having electrodes and a reagent layer thereon. The base substrate and covering layer define a sample receiving chamber that draws fluid sample therein by capillary action, whereupon the fluid sample reacts with the reagent in the chamber. A voltage or potential is controlled or applied across the electrodes, and the current generated is measured at one or more times and is then correlated to analyte concentration. "Coulometric" and "potentiometric" techniques are also known in which charge or potential, respectively, instead of current is measured and correlated to analyte concentration.

Various techniques are known in the art to form the electrical patterns in electrochemical biosensors. For instance, screen printing is a wet material technique that generally allows reliable formation of electrode structures and patterns having a gap width or feature size of approximately 75 µm or greater.

Laser scribing usually employs a high power excimer laser, such as a krypton-fluoride excimer laser with an illumination wavelength of 248 nm, to etch or scribe individual lines in a conductive surface material and to provide insulating gaps between residual conductive material which forms electrodes and other desired components. The scribing is accomplished by moving the laser beam across the surface to be ablated, and such a technique can be undesirably time consuming if a complex electrical pattern is to be formed on the surface.

Broad field laser ablation is a technique that has recently been employed to manufacture electrochemical biosensors having incredibly accurate and highly defined electrical patterns with additional functionalities that have hitherto been unavailable. Examples of such electrochemical biosensors can be found in U.S. Pat. No. 7,073,246, U.S. Patent Publication Nos. 2005/0103624, 2006/0200981, and 2006/0200982, the disclosures of which are hereby incorporated by reference. Publication No. 2005/0103624 discloses a high degree of accuracy and definition with which electrical patterns can be formed with laser ablation. Similarly, U.S. Patent Publication No. 2005/0023137, which is also hereby incorporated herein by reference, discloses biosensors with incredibly small and complex electrical patterns that provide a large footprint on the base substrate for other components, such as a display and power supply, among others. Other known techniques involving lasers include laser induced forward transfer, or LIFT, such as is disclosed in U.S. Pat. Nos. 6,177,151 and 4,752,455, and PCT/US/2006/035312, each of which is hereby incorporated by reference herein.

It would be desirable to further improve the electrical patterns and method of making the same in electrochemical biosensors.

SUMMARY OF THE INVENTION

The present invention provides a novel electrochemical biosensor and an inventive method of making the same. In one embodiment there is provided a biosensor for determining presence or concentration of an analyte in a fluid sample. The biosensor has a substrate having an electrical pattern formed thereon that includes a working electrode, a counter electrode, contact pads, and traces electrically connecting the working and counter electrodes to their respective contact pads. One or more of a spacing layer and a covering layer overlies and cooperates with the substrate to define a chamber for receiving a fluid sample. The inventive biosensor includes a first region in which the electrical pattern is formed of a first electrically conductive material and a second region in which the electrical pattern is formed of a second electrically conductive material. At least one of the traces includes a first section located in the first region electrically connected to a second section located in the second region, the first and second sections being comprised of the first and second electrically conductive materials, respectively.

In particular embodiments, it is advantageous to provide the electrical patterns of the first and second regions in an overlapping arrangement, which is to say that part of the electrical pattern will overlap the other at the transition from region to region. At the transition point, the overlapped portion may be slightly thicker than the remainder of the pattern. In other embodiments, the transition from one region to another can be made by abutting the electrical patterns against one another at the transition, or by having one of the regions become gradually thinner across the transition while the other becomes gradually thicker, the net thickness over the transition remaining substantially the same. In yet other embodiments it may be desirable to form a seed layer to obtain a good connection between overlapping conductive materials, as described in more detail below.

Biosensors in accordance with these teachings typically comprise a generally thin and flat biosensor body having a length greater than its width, a dosing end where the electrodes are typically located, and a meter insertion end where the contact pads are typically located. The biosensor body has at least two regions in which the electrical pattern is formed of different electrically conductive materials. The dosing end is located in one of these regions and the meter insertion end is located in the other. The traces thus typically span the regions in order to electrically connect each electrode with its respective contact pad.

For example, in many embodiments it is desirable to provide the electrical features that are located in the sample receiving chamber with very high-quality electrically conductive material which is also not negatively affected by the presence of biological components and/or the particular reagent chemistry present in the sample receiving chamber. Noble metals such as gold, platinum and palladium are suitable conductors for this purpose and can therefore be provided in the region of the biosensor that includes the sample receiving chamber. On the other hand, other regions of the biosensor which do not include the sample receiving chamber need not be provided with a material as expensive or as susceptible to scratching and damage as noble metals, and a substantially more robust conductive material may be used in these regions. For example, copper is a suitable material choice for the electrical pattern in a region extending from the meter insertion end of the biosensor toward the region which includes sample receiving chamber.

Similarly, in another embodiment, the region of the biosensor that includes the contact pads can be provided with a material such as indium oxide doped with tin oxide (ITO), which has been shown to have suitable electrical conductive properties, but is also suitably robust in order to be resistant to scratching. It should be appreciated that if a contact pad on a biosensor is scratched and degraded as it is inserted into the meter, the resistance of the biosensor may be affected and in turn the accuracy of the test result may be compromised. Providing the electrical pattern at the meter insertion end of the biosensor with ITO or copper, for example, as the conductive material addresses this problem.

Typically, the regions of the biosensor are positioned side by side along a lengthwise direction of the biosensor. For example, the portion of the electrical pattern located at the meter insertion end of the biosensor is formed from one electrically conductive material, the portion of the electrical pattern located at the dosing end is formed from a second electrically conductive material, and the region therebetween can be formed of yet a third electrically conductive material, if desired.

In another form thereof, these teachings provide inventive methods for mass producing electrical patterns that are used in biosensors like those just described. In one such method, an electrically insulating base material is provided. First and second different electrically conductive materials are deposited on a portion of the base material substantially side by side to one another. A plurality of electrical patterns is formed on the portion of the base material, and each electrical pattern includes a first region formed from the first electrically conductive material electrically connected to a second region formed from the second electrically conductive material. The first region of the electrical pattern comprises at least one electrical feature, for example, an electrode.

In one exemplary embodiment, the depositing step comprises depositing a layer of the first electrically conductive material on the portion of the base material and depositing a second layer of the second electrically conductive material on the portion of the base material substantially side by side to and in electrical contact with the first layer. In one exemplary production method, this layered portion of base material can be rolled onto a supply roll and provided as a "production-ready" material to a manufacturing process. This material is then unrolled and portions of the first and second layers are removed to form the electrical patterns having two regions electrically connected to one another. In particular embodiments, broad field laser ablation is used to remove the conductive material to form the electrical patterns. Broad field laser ablation advantageously allows several complete electrical patterns to be formed in a single step, all at once, or in a succession of steps, as desired. It also allows great precision and detail in the electrical patterns formed thereby. However, many other methods for removing the conductive material can be used to form the electrical patterns, such as photo etching, plasma assisted chemical etching, laser scribing and many others.

In another embodiment, multiple layers or "stripes" of material can be deposited on the base material, typically in the form of a repeating pattern. The base material can then be divided or cut into smaller portions of substantially identical production ready material like just described. This material can then be rolled up into rolls and sent to a further production station where the rolls will be unrolled, have portions of their conductive layers removed to form electrical patterns, and then further processed into finished biosensors. Thus, depending upon the particular requirements, the base material can be formed with as little as only two side by side layers of different conductive materials to a hundred or more side by side layers, typically in a repeating pattern.

In yet another embodiment, the inventive electrical patterns are formed directly on the base material by a technique such as laser induced forward transfer ("LIFT") or similar techniques known in the art. In such a technique, further removal of conductive materials to form the electrical patterns is unnecessary. Instead, the conductive material in the shape of the desired electrical pattern is transferred directly, typically from a laser transparent substrate, to the base material. In one embodiment incorporating this technique, a broad field laser beam is projected through a mask having an opening in the shape of a portion of the electrical pattern, whereby a portion of the conductive material in the shape of the pattern is removed from a thin film of the same and transferred to the base material. Thus, in this embodiment, the electrical pattern or a portion thereof takes its shape before the transfer of the conductive material to the substrate is completed. A similar technique can be used to directly transfer additional regions of the electrical pattern to the base material.

Once the electrical patterns are formed on the portions of base material, further processing steps are utilized to complete the assembly of the biosensors. Typically, a reagent is coated or deposited on or over at least a portion of one or more of the electrodes of the electrical patterns, the reagent usually covering at least a portion of the working electrode. A covering layer and/or a spacing layer is then laminated over the portion of the base material, thereby forming a cover and defining a sample receiving chamber for each individual biosensor to be formed. Finally, cutting tools are used to cut through the covering layer, spacing layer and the base material to form individual biosensors in a mass production fashion. As noted, the electrical pattern of each individual biosensor will include at least two regions in which the material composition of the electrical patterns is different, the advantages of which have been noted above and will become more apparent below and in reference to the attached Figures.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
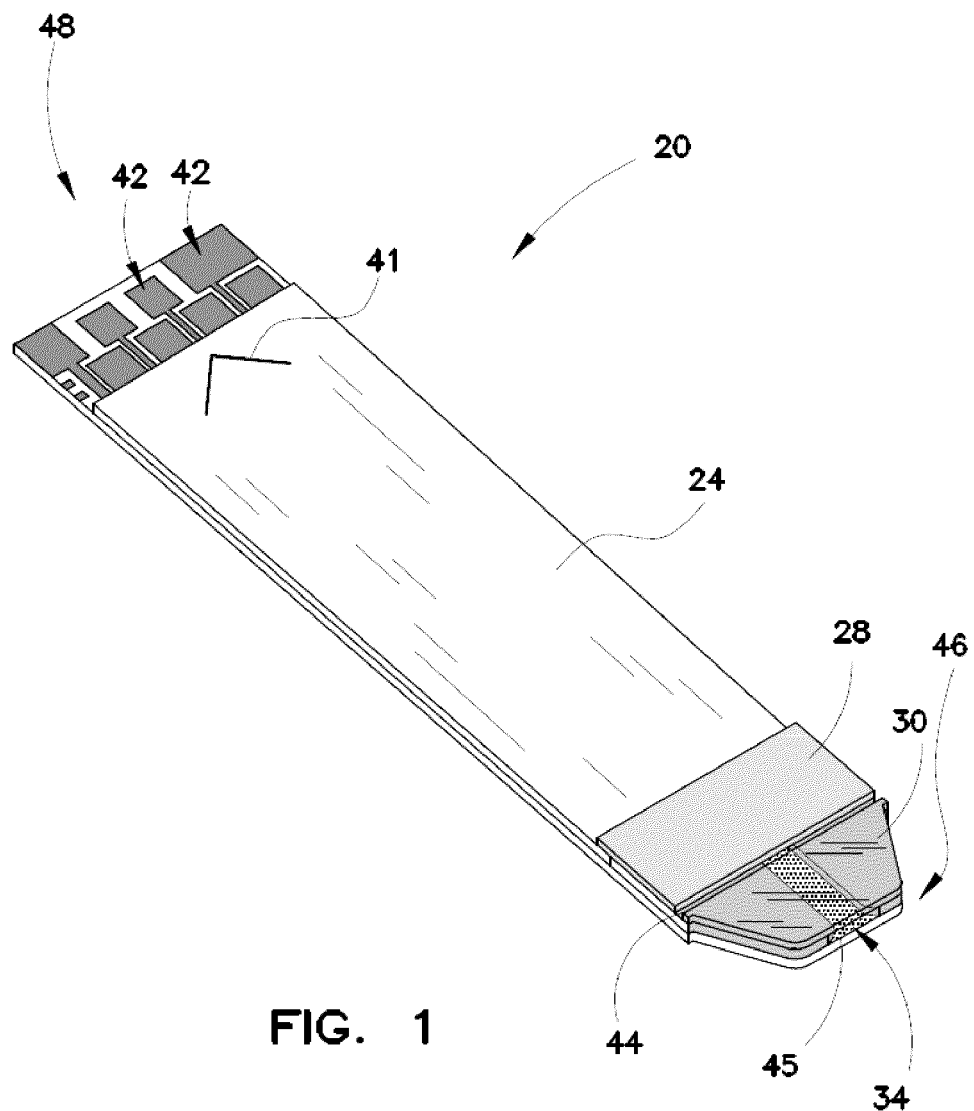
FIG. 1 is a perspective view of a biosensor formed in accordance with these teachings.
Figure 2:
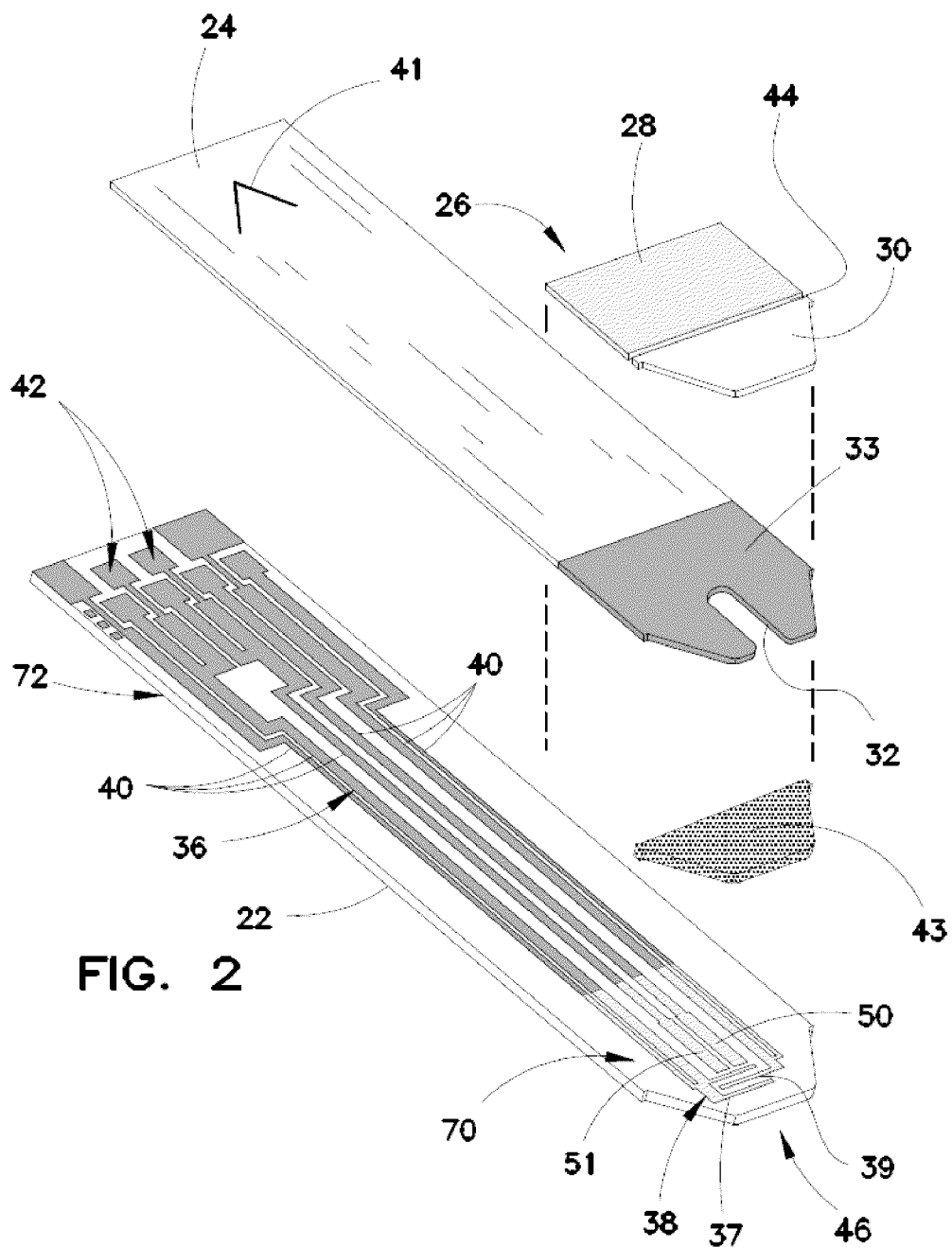
FIG. 2 is an exploded perspective view of the biosensor shown in FIG. 1.

Turning now to FIGS. 1 and 2, there is shown an embodiment of a biosensor useful in accordance with the present teachings. Biosensor 20 includes a base substrate 22, a spacing layer 24 and a covering layer comprising body cover 28 and chamber cover 30. The spacing layer 24 includes a void portion 32 to provide a sample-receiving chamber 34 extending between the base substrate 22 and the covering layer. An alternative covering layer could comprise a top cover (not shown) overlying the spacing layer 24 and including a vent hole (not shown) in fluid communication with the sample-receiving chamber 34.

The base substrate 22 carries an electrical pattern 36 including a plurality of electrodes 38 including at least a working electrode 39 and counter electrode 37. Electrical pattern 36 also includes electrode traces 40 terminating in contact pads 42. The electrodes 38 are positioned within the sample-receiving chamber 34. In one embodiment, electrodes 38 include separate working and counter electrodes 50, 51 for detecting dosing sufficiency before a measurement sequence can begin. As described in more detail below, e.g., with reference to FIGS. 11 and 12, various other configurations of electrical patterns may be formed in accordance with these teachings, depending upon the particular electrical features desired for the biosensor. A suitable reagent system 43 (FIG. 2) overlies at least a portion of one of the electrodes, particularly the working electrode, and is shown in FIG. 2 overlying electrodes 37, 39, and a portion of electrodes 50 and 51 within the sample-receiving chamber.

The body cover 28 and the chamber cover 30 overlying the spacing layer 24 have a gap 44 therebetween, which defines a vent opening communicating with the sample-receiving chamber 34 to allow air to escape the chamber as a sample fluid enters the chamber from the edge opening or fluid receiving opening 45 (FIG. 1). Biosensor 20 includes a dosing end 46 and a meter insertion end 48. The dosing end is typically distinguishable from the meter insertion end so as to aid users. For example, the biosensor of FIG. 1 has a beveled dosing end 46, and it provides a color contrast between the dosing end and the remainder of the biosensor. One or both of these are sufficient examples of how to distinguish the dosing end from the meter insertion end. In addition, strip graphics can be used to further improve the intuitiveness of the strip design; e.g., arrow 41 indicates the direction of insertion of the strip into the meter.

Turning now to FIG. 2 in particular, the biosensor includes a base substrate 22 which comprises an insulating material supporting the electrical pattern 36 and other components of a biosensor. Typically, plastics such as vinyl polymers, polyimides, polyesters, and styrenes provide the electrically insulating and structural properties which are required. Further, for embodiments of a biosensor 20 according to the present teachings that are mass producible from rolls of material, as discussed in greater detail below, it is desirable that the material properties be appropriate to have sufficient flexibility for roll processing, while also giving a useful stiffness to the finished biosensor. The insulating material of base substrate 22 can be selected as a flexible polymeric material such as polyester, especially high temperature polyester materials; polyethylene naphthalate (PEN); and polyimide, or mixtures of two or more of these. Polyimides are available commercially, for example under the trade name Kapton®, from E.I. duPont de Nemours and Company of Wilmington, Del. (duPont). A particularly suitable base substrate insulating material is MELINEX® 329 available from duPont.

The electrodes 38, e.g., at least the measuring electrodes comprising a working electrode 39 and a counter electrode 37, are at least partially exposed within the sample-receiving chamber 34. The sample-receiving chamber is configured such that sample fluid entering the chamber is placed in electrolytic contact with both the working electrode 39 and the counter electrode 37. This allows electrical current to flow between the measuring electrodes 38 upon the electrooxidation or electroreduction of the analyte resulting from an electrical potential or voltage being applied or controlled between the electrodes 38.

These teachings disclose a biosensor having two or more regions in which the electrical pattern 36 is formed from different conductive materials. For example, FIG. 2 shows two general regions 70 and 72. In one embodiment, the electrical pattern 36 in region 70, which includes electrical features such as electrodes 38 (e.g., working and counter electrodes 37, 39 and dose sufficiency electrodes 50, 51) and at least a portion of one or more of the electrode traces 40, can be formed from a noble metal such as gold, silver, palladium, or platinum, as is indicated by a light shade of gray illustrated in FIG. 2. For typical embodiments comprising an analyte biosensor, since region 70 contains the reagent that reacts with the fluid sample when the biosensor is dosed and the electrochemical reaction occurs there, this region in certain embodiments is formed with a sensitive, premium conductive material such as a noble metal.

On the other hand, the remainder of the electrical pattern 36 comprising region 72 may not require a premium conductor in certain embodiments. Thus, a more robust material such as copper, indium-tin oxide, or carbon ink, may form the electrical pattern in region 72 in the embodiment illustrated in FIG. 2. As will become more apparent with reference to the description of the method of production presented below, this disclosure teaches a wide variety of options for forming two or more regions in a biosensor, each region having different electrically conductive material in the electrical pattern. The selection of the material for each region typically depends on the specifications and/or uses for the biosensor, and may be optimized as needed or desired, according to the knowledge and skill of a person of ordinary skill in the art. The transition between regions typically occurs in the traces, such that each trace has one segment or section formed from the conductive material of one region and a second segment or section formed from the conductive material of the other region.

Figure 3:
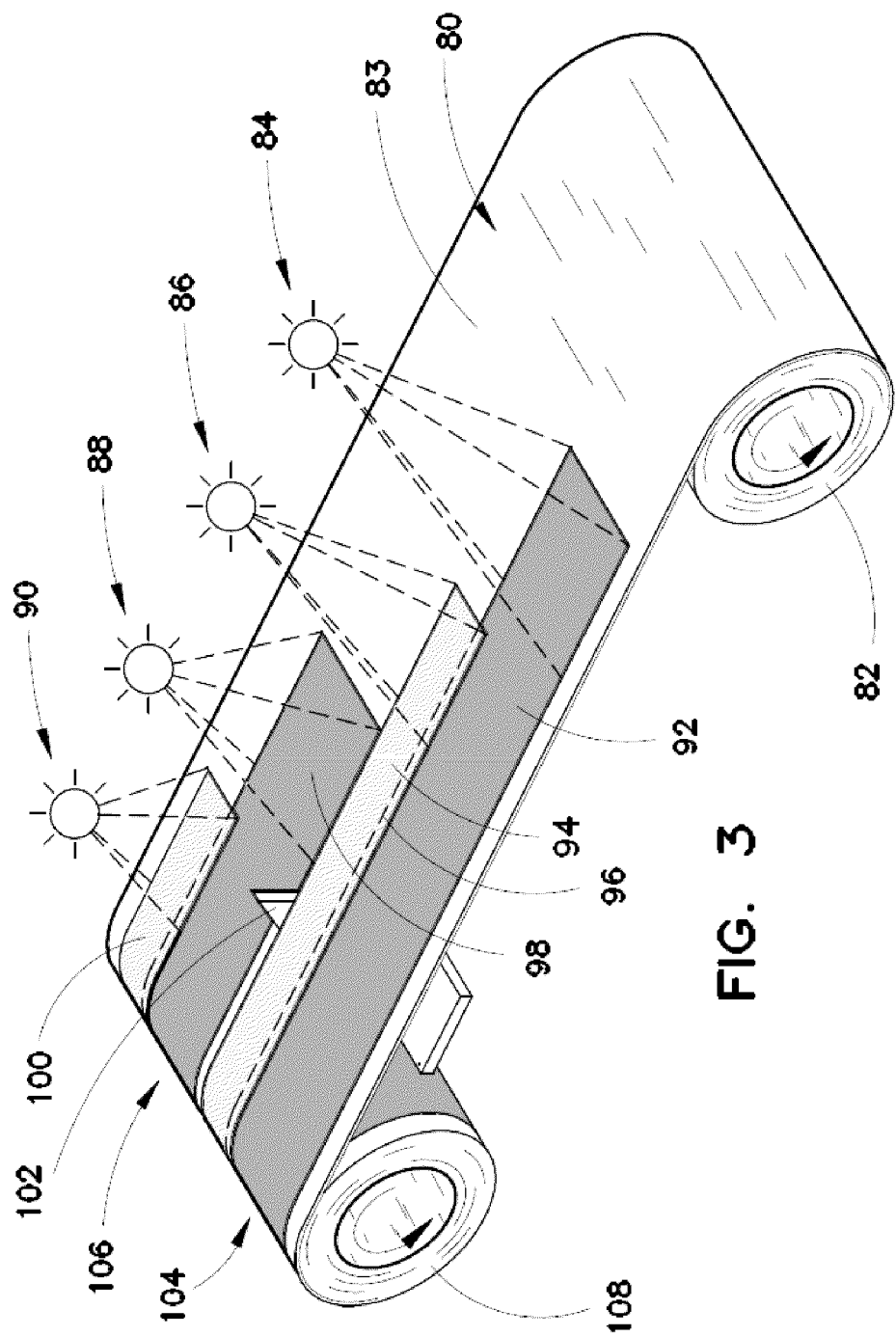
FIG. 3 is a perspective view schematically illustrating the depositing of multiple side by side layers or films of conductive material on a base material.

Turning now to FIG. 3, one exemplary method of mass producing the electrical patterns 36 for electrochemical biosensors can be appreciated. In this exemplary embodiment, a flexible and substantially flat base material 80 is provided on a supply roll 82. Base material 80 on roll 82 has been pretreated as desired to clean or modify the surface 83 and make it ready to receive conductive layers, as is known in the art. As material 80 is unrolled, it passes through successive processing stations 84, 86, 88 and 90 shown schematically in FIG. 3. In these processing stations thin films or layers of conductive material are deposited or applied side by side, but may be allowed to overlap to a certain extent. The extent to which the layers are offset or overlap, if at all, can be varied depending upon the particular application and/or desired electrical specifications or effects. In one embodiment, the degree of overlap or offset is maintained substantially uniform along the entire length of the insulating material 80 in order to, as will be appreciated from the description below, form biosensors substantially identically with respect to electrical properties within the roll and from roll to roll.

In the illustrated embodiment of FIG. 3, for example, at station 84, a thin conductive film or layer 92 is shown being deposited on surface 83. At station 86, a layer or film 94 of a conductive material different from layer 92 is deposited adjacent to layer 92 such that layer 94 overlaps layer 92 as indicated by dashed line 96. At stations 88 and 90, layers 98 and 100 are deposited in the same manner as layers 92 and 94, respectively. Further, in this embodiment, layers 92 and 94 are the same width as layers 98 and 100, respectively, the advantages of which will become apparent. In this embodiment, layer 98 is applied such that there is minimal if any overlap with layer 94. This is because once it has passed the processing stations 84, 86, 88, 90, the base material 80 is cut with knife 102 as shown to form two identical smaller portions 104 and 106 each comprising a production-ready base material, which are rolled onto two take-up spools, one of which is illustrated in FIG. 3 at reference numeral 108. There need be no electrical conductivity between layers 94 and 98 since they are ultimately separated by cutting, and overlap of these layers is therefore unnecessary. Layers 92 and 100 may be applied to the opposite lateral edges, respectively, of surface 83 or may be applied such that a small band of uncovered material remains at the edges as shown. Further trimming may or may not be necessary depending on the particular biosensor design.

It should be understood that the "stations" shown in FIG. 3 can represent any of a wide variety of techniques for applying the conductive layers. Examples of suitable techniques include but are not limited to sputtering, physical vapor deposition (PVD), plasma assisted chemical vapor deposition (PACVD), chemical vapor deposition (CVD), electron beam physical vapor deposition (EBPVD), and/or metal-organic chemical vapor deposition (MOCVD). Vapor deposition is typically performed under vacuum. These techniques are well known in the art and can be used to selectively provide uniformly thin coatings of metal or other conductive materials onto a substrate as depicted in FIG. 3. The resulting base material can be inspected to ensure that the conductive coatings or layers are uniform and free of material defects.

Further, while the stations 84-90 are shown set up one after the other in FIG. 3, one of skill in the art would readily recognize many variations for forming the conductive layers. For example, the conductive material depositing stations can be positioned in about the same location and the roll 82 indexed back and forth. During each pass a different conductive layer would be applied. Other variations are possible.

As suggested above, many conductive materials can be used for the layers shown in FIG. 3, depending upon the particular application for the biosensor. The conductive layers may contain pure metals, alloys, or other conductive materials such as carbon inks and the like. Examples of suitable conductors include: aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or solid solutions of these materials. Indium tin oxide (ITO) is a conductor material which can be used on the meter insertion end of the biosensor, as described in more detail below. In other embodiments, materials can be selected to be essentially unreactive to biological systems; such materials include: gold, platinum, palladium, iridium, or alloys of these metals. The conductive layer may be any desired thickness.

Further, one of skill in the art would recognize that certain selected combinations of conductive materials for adjacent regions may require a so-called "seed layer" to ensure good physical adherence and structural and chemical stability between the two layers at the transition between regions, i.e., where the layers either abut or overlap. For example, if the two regions are formed from copper and gold, respectively, one approach would be to first deposit the copper layer on the base material, then apply a seed layer of, e.g., chromium, titanium nitride or aluminum nitride on the copper at the location where the gold layer will abut or overlap the copper, and then apply the gold layer. The use of seed layers is known in the art and examples of the same are disclosed in U.S. Pat. No. 6,822,176, which is hereby incorporated herein by reference.

Figure 3A:
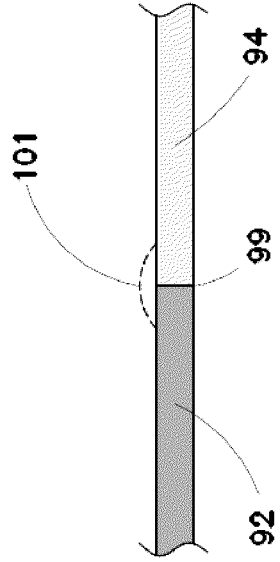
FIGS. 3A-3D are fragmentary side views showing various arrangements of the transition region between two side by side layers of different electrically conductive materials.
Figure 3C:
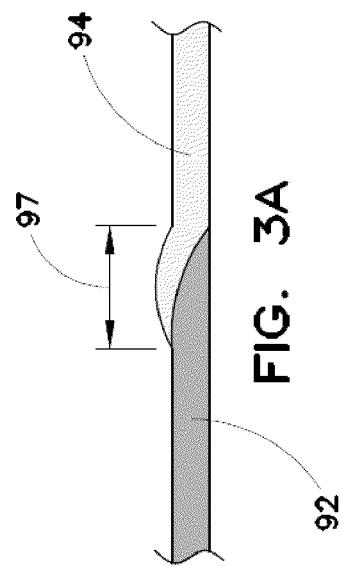
Figure 3B:
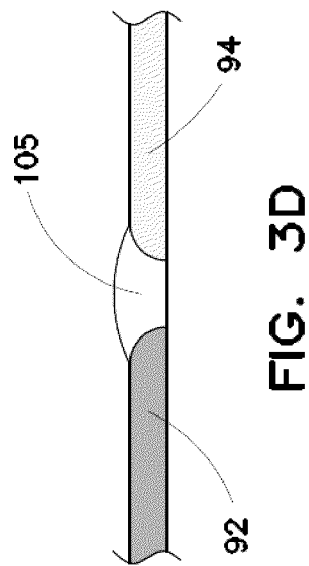

If an overlapping arrangement is employed, it is envisioned that the width of the overlap need only be a few millimeters, e.g., from 1 to 3 mm, typically on the order of about 2 mm. In embodiments in which an overlapping arrangement is employed, it is generally desirable to provide sufficient overlap to ensure that the layers are continuously connected along their length despite deviations in layer width due to manufacturing limitations. Of course, the electrical pattern may be thicker in the region of any such overlap. FIG. 3A, for example, illustrates an overlap region or transition 97 of conductive layers 92 and 94 in which the arrangement of layers is thicker in the overlap region 97. As discussed above, the layers can also be formed in an abutting relationship as illustrated in FIG. 3B, in which layers 92 and 94 abut one another as shown at reference numeral 99. It may be desirable in some circumstances to include an additional conductive seam layer 101 (shown in phantom in FIG. 3B) to allow for possible gaps between the two layers arising from manufacturing limitations in forming an abutting joint.

Figure 3D:
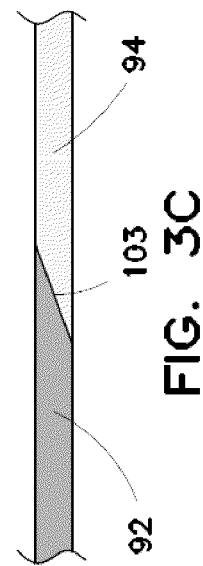

One of skill in the art would recognize other means for electrically connecting the adjacent conductive layers. For example, the deposition technique may be such that one layer becomes thinner while the other becomes thicker traversing the region of overlap, such that the overall thickness over the transition between the two regions remains roughly the same, e.g., as shown at reference numeral 103 in FIG. 3C. Stated another way, the deposition technique used to form the transition shown in FIG. 3C is one in which both layers are thinner at their edges. It is also possible to form the layers spaced apart initially and then electrically join them by applying a third conductive material between them, e.g., as shown in FIG. 3D, in which the conductive seam layer 105 joins layers 92 and 94. This approach may prove especially useful when it is desired to electrically connect two conductive material layers that are not physically or chemically compatible when directly contacting one another, as discussed above with regard to seed layers. One of skill in the art would recognize from this disclosure various other possibilities for forming the transition between the two conductive regions, all of which are considered within the spirit and scope of this disclosure.

Figure 4:
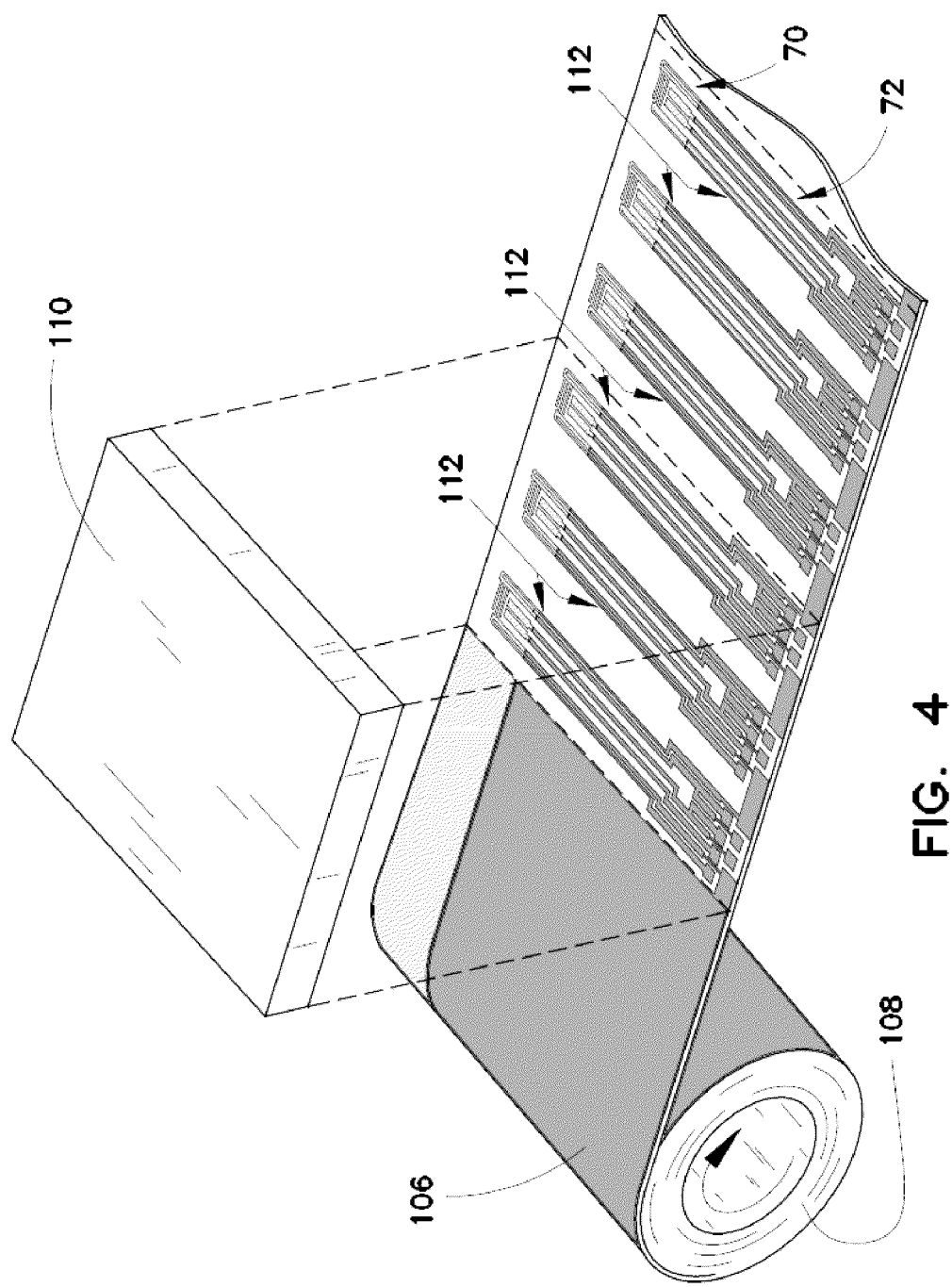
FIG. 4 is a fragmentary perspective view illustrating the forming of electrical patterns on a portion of the base material of FIG. 3 to form a base substrate web.

Turning now to FIG. 4, the production-ready base material 106 formed as shown in FIG. 3 is now unwound in a different process stage and advanced through a laser ablation apparatus 110 shown diagrammatically in FIG. 4. A laser apparatus and process suitable with these teachings is described in U.S. Pat. No. 7,073,246 and U.S. Publication No. 2005/0103624, incorporated by reference above. In exemplary embodiments, the laser apparatus performs broad field laser ablation with a sufficiently large projection to ablate the conductive material in order to form several electrical patterns 112 in a single step. In the particular example illustrated in FIG. 4, base material 106 is indexed such that three electrical patterns are formed in a single step by removing portions of the conductive material from the base material except where the electrical patterns are to be defined. As shown, conductive material is removed such that two regions 70 and 72 of each electrical pattern 112 having different electrically conductive material are formed. The resulting structure is a base substrate web 107 (FIG. 5) that can be further processed for purposes of manufacturing a plurality of biosensors.

Figure 5:
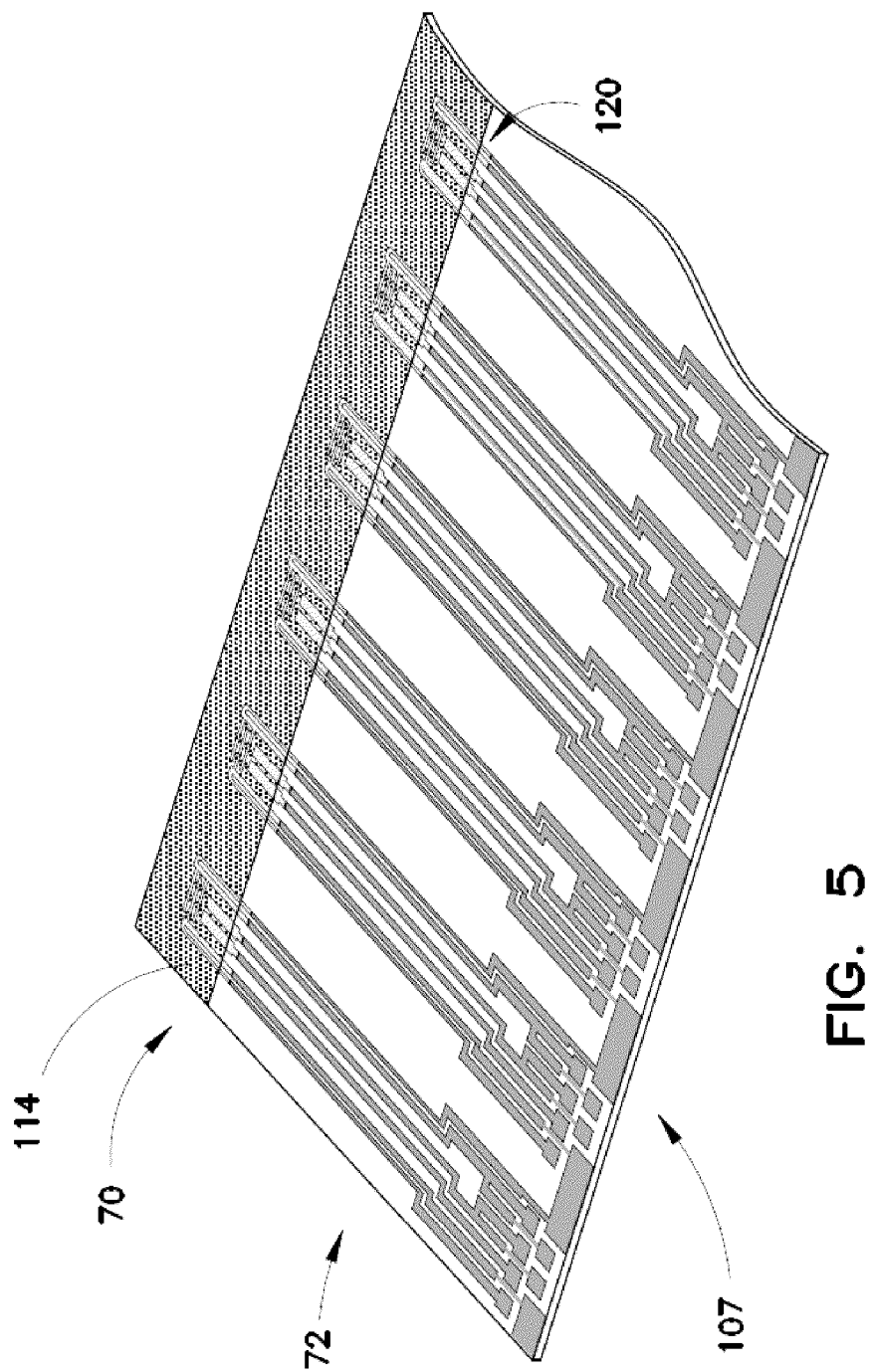
FIG. 5 is a perspective view of a biosensor base substrate web having a reagent layer or stripe applied thereto.

In one embodiment, the base substrate web 107 is further processed by adding a layer 114 of reagent material as shown in FIG. 5. Suitable compositions for reagent layer 114 and the method of applying it are disclosed in U.S. Publication No. 2005/0016844, which is incorporated herein by reference, and need not be repeated in detail herein. Briefly, the reagent layer may be applied by any number of suitable dispensing techniques such as curtain coating, hot melt coating, rotary screen coating, doctor blade or air knife coating, Meyer bar coating, and reverse roll coating techniques. The reagent layer 114 is typically deposited on the base substrate web 107 as a wet composition at a thickness of between about 50 μm and about 100 μm. In the embodiment shown in FIG. 5, to ensure that the reagent layer 114 only contacts the conductive material in region 70 (which may be a noble metal), and to allow for manufacturing tolerances in the application of layer 114, a portion 120 of region 70 may extend beyond or protrude from under the reagent layer 114 as shown. After the reagent layer is applied, the various other layers, such as spacing layer 24 and the covering layer are assembled, typically with roll processing techniques as described in U.S. Publication No. 2005/0016844 to form completed biosensors such as are illustrated in FIGS. 1 and 2.

It should be readily recognized that many variations for forming and cutting the base material into the smaller, production-ready base materials, if desired, as well as the number, location and material composition of the different regions of electrical patterns on the biosensors themselves are possible.

Figure 6:
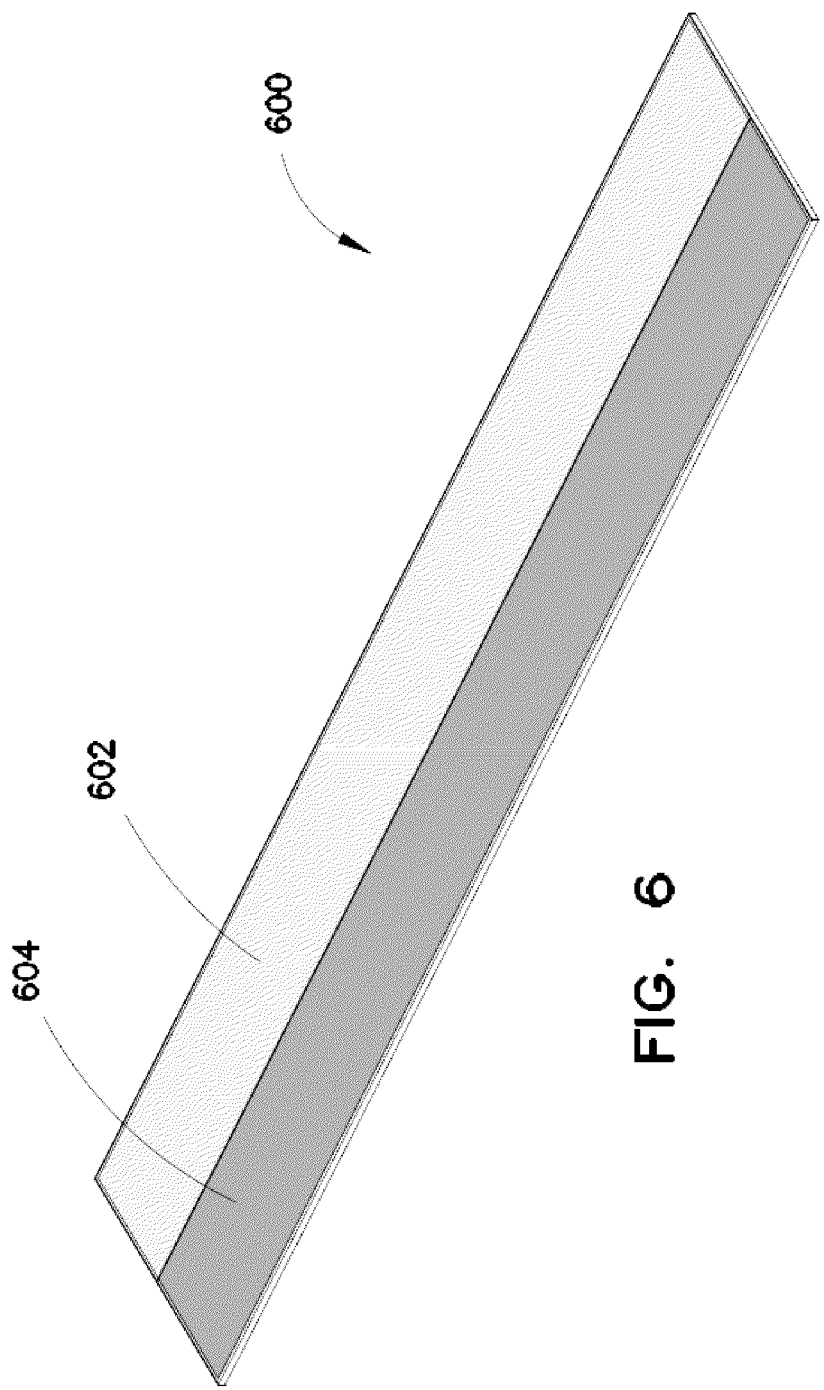
FIGS. 6-9 are perspective views of various base materials from which the electrical patterns of multiple biosensors can be formed.

For example, FIG. 6 illustrates one embodiment in which the base material 600 can be formed with only two electrically conductive layers 602 and 604 positioned substantially side by side and in electrical communication with one another. Base material 600 can be formed as described above with reference to FIG. 3 with only two processing stations or passes, and then be provided directly to a production process much like that discussed above with respect to FIG. 4 for forming the base substrate web 107 without cutting beforehand. That is, base material 600 is initially provided as a production-ready base material, in contrast to the base material 80 of FIG. 3 which is cut down into production-ready lots of base material 104, 106.

Figure 7:
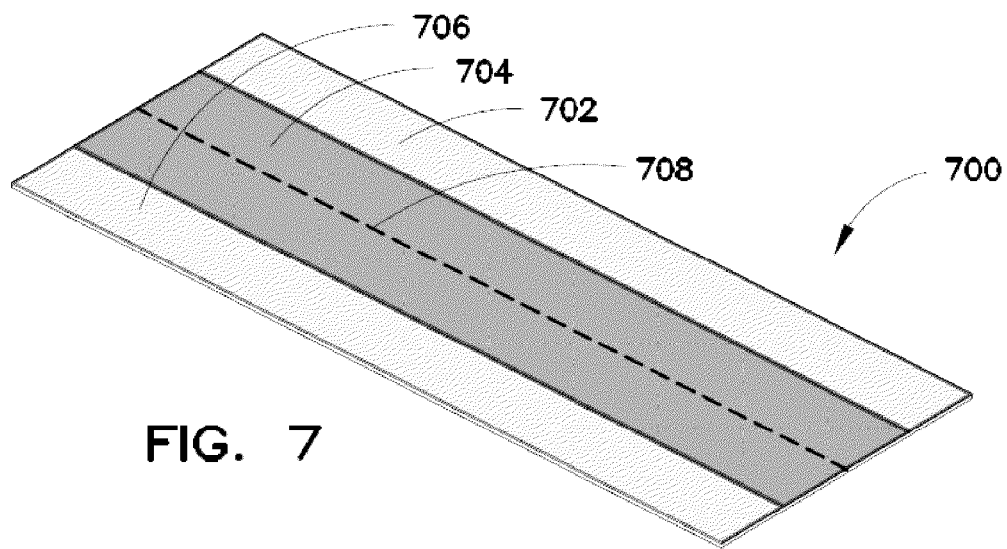

Alternatively, FIG. 7 shows a base material 700 having 3 conductive layers 702, 704 and 706 formed thereon by, e.g., a process similar to that shown and described with reference to the description of FIG. 3. Layers 702 and 706 are comprised of the same electrically conductive material and layer 704 is formed of a different electrically conductive material that can be cut along dashed line 708 to form two identical production-ready lots of base material. Such an arrangement essentially allows two layers to be formed in a single step (i.e., layer 704 is divided in half and ultimately becomes two layers in different production lines) and thus provides certain efficiencies.

Figure 8:
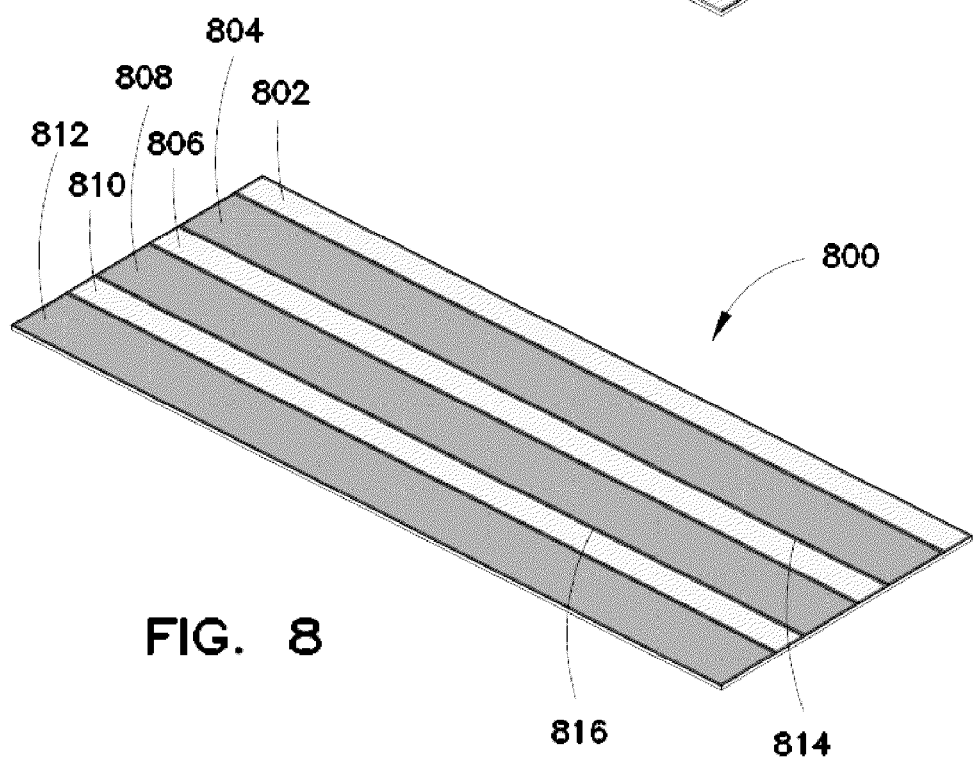

FIG. 8 illustrates a multilayer base material 800 having repeating layers or "stripes." Layers 802, 806 and 810 are formed of the same conductive material and have substantially the same width. Layers 804, 808 and 812 are also all formed of the same conductive material (different than layers 802, 806, and 810) and have substantially the same width. Three lots of production-ready base material can thus be formed by making two cuts along lines 814 and 816, respectively.

Figure 9:
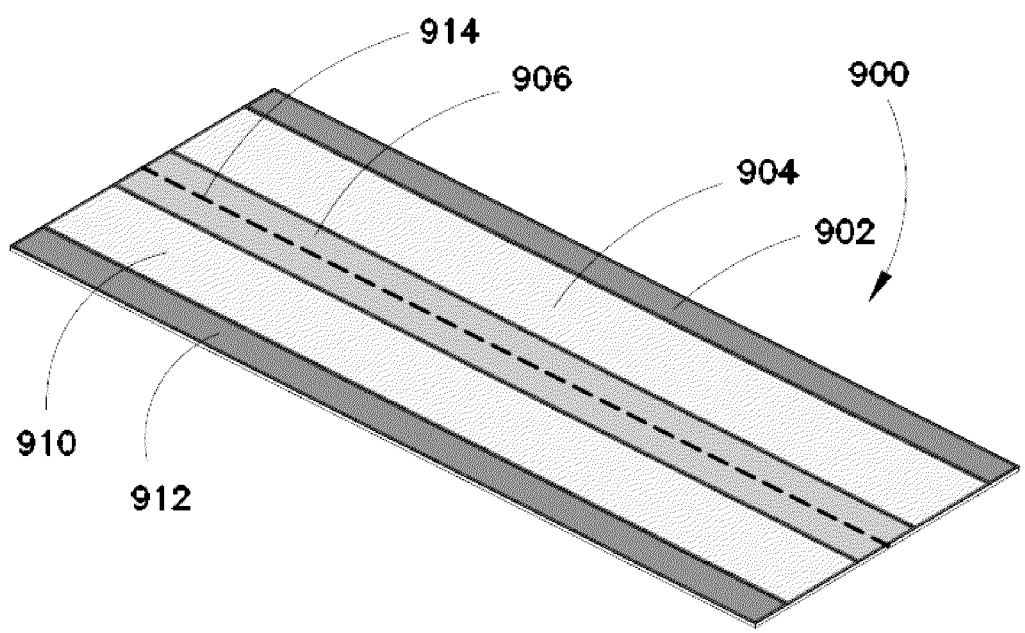

FIG. 9 shows a base material 900 having five conductive layers 902, 904, 906, 910 and 912 formed thereon by, e.g., a process similar to that shown with reference to the description of FIG. 3. Layers 902 and 912 are comprised of the same electrically conductive material and layers 904 and 910 are comprised of the same electrically conductive material, different than layers 902 and 912. Layer 906 is formed of a third different electrically conductive material. The base material 900 can be cut along dashed line 914 to form two identical lots of production-ready base material, each having three layers or stripes extending substantially side by side.

It should be readily recognized from these teachings that that the number of repeating layers or stripes and their configuration on the base material (before it is cut into production-ready lots, if needed) can be varied as desired as a function of manufacturing efficiency and the desired number and type of regions in the electrical pattern of the biosensors to be formed. For example, it is envisioned that base materials useful in large scale production using these teachings could be as wide as five (5) feet or more and include 100 or more side by side layers or stripes. Many cuts would obviously then be made to this striped base material to reduce it into multiple lots of production-ready base material that would be further processed.

Figure 10A:
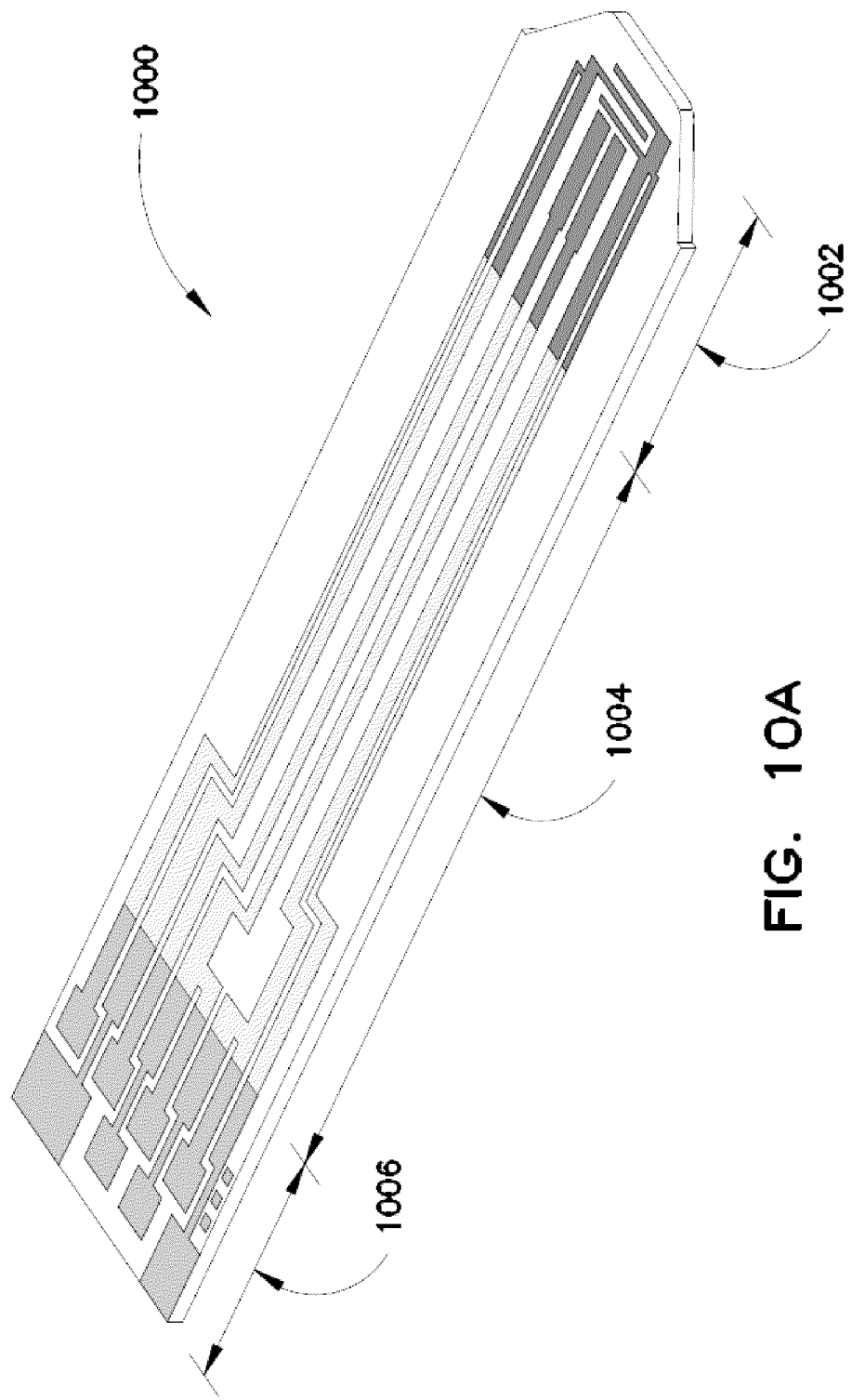
FIG. 10A is a perspective view of a biosensor substrate having an electrical pattern of three different conductive materials formed thereon.

With reference to FIG. 10A, a biosensor base substrate 1000 is shown formed from a base substrate web formed from one of the portions of base material formed as described with reference to FIG. 9. The base substrate 1000 has three regions 1002, 1004 and 1006 in which the electrical pattern comprises a different conductive material. However, it should be recognized that embodiments in which three or more electrical pattern regions are provided, it may be desirable to have some regions with the same conductive material. For example, in a biosensor comprising a base substrate configured like base substrate 1000, it may be desirable to have the regions 1002, 1006 at the two ends formed of the same material and the middle region 1004 formed of a different material. While a virtually endless variety of material compositions could be employed for a base substrate 1000 having an electrical pattern comprising three regions, one exemplary embodiment would include region 1002 formed of a noble metal such as gold or platinum, region 1004 formed of a good conductor such as copper, and region 1006 formed of a robust material that is resistant to scratching (e.g., when the completed biosensor is inserted into a meter) such as ITO.

Figure 10B:
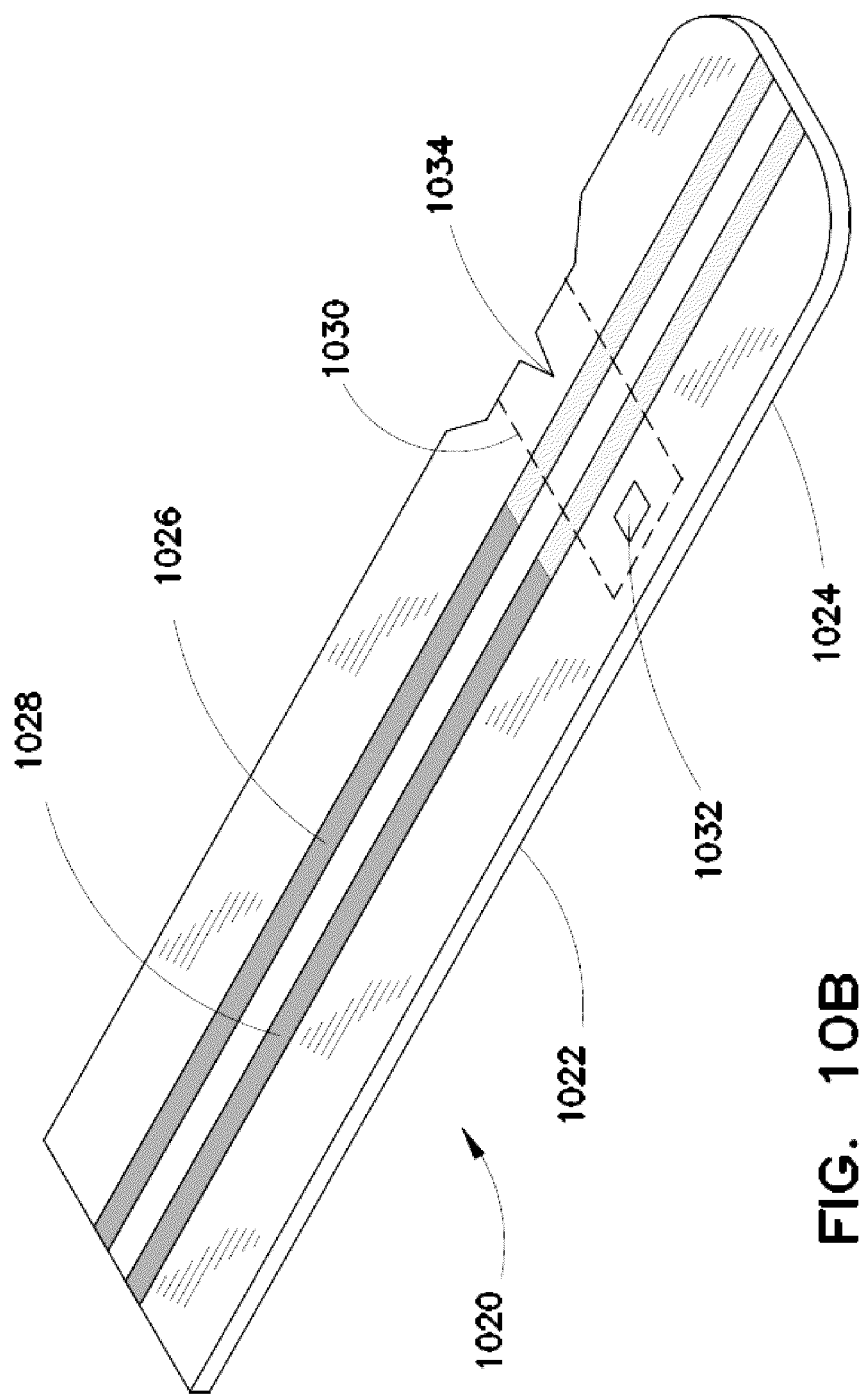
FIG. 10B is a perspective view of a biosensor substrate in accordance with an alternate embodiment.

It should also be understood that, while the electrical patterns and their formation described above have been rather sophisticated, these teachings can advantageously be employed for a wide variety of electrical patterns that are employed in biosensors. For example, FIG. 10B illustrates a biosensor base substrate 1020 having two regions 1022 and 1024 in which the conductive tracks 1026 and 1028 of the electrical pattern comprise different conductive materials. This embodiment illustrates that the electrical patterns for which these teachings can be utilized can be quite simple, in this case comprising merely two conductive tracks. The base substrate 1020 forms part of a "side fill" biosensor having a capillary chamber in the area shown by dashed line 1030. A vent hole 1032 for the capillary chamber and a notch 1034 is provided to aid in filling the chamber with sample fluid. Aside from the regions of the electrical pattern formed from different conductive materials, such a biosensor is known in the art and an example of the same can be found in U.S. Pat. No. 6,270,637, which is hereby incorporated herein by reference.

Figure 11:
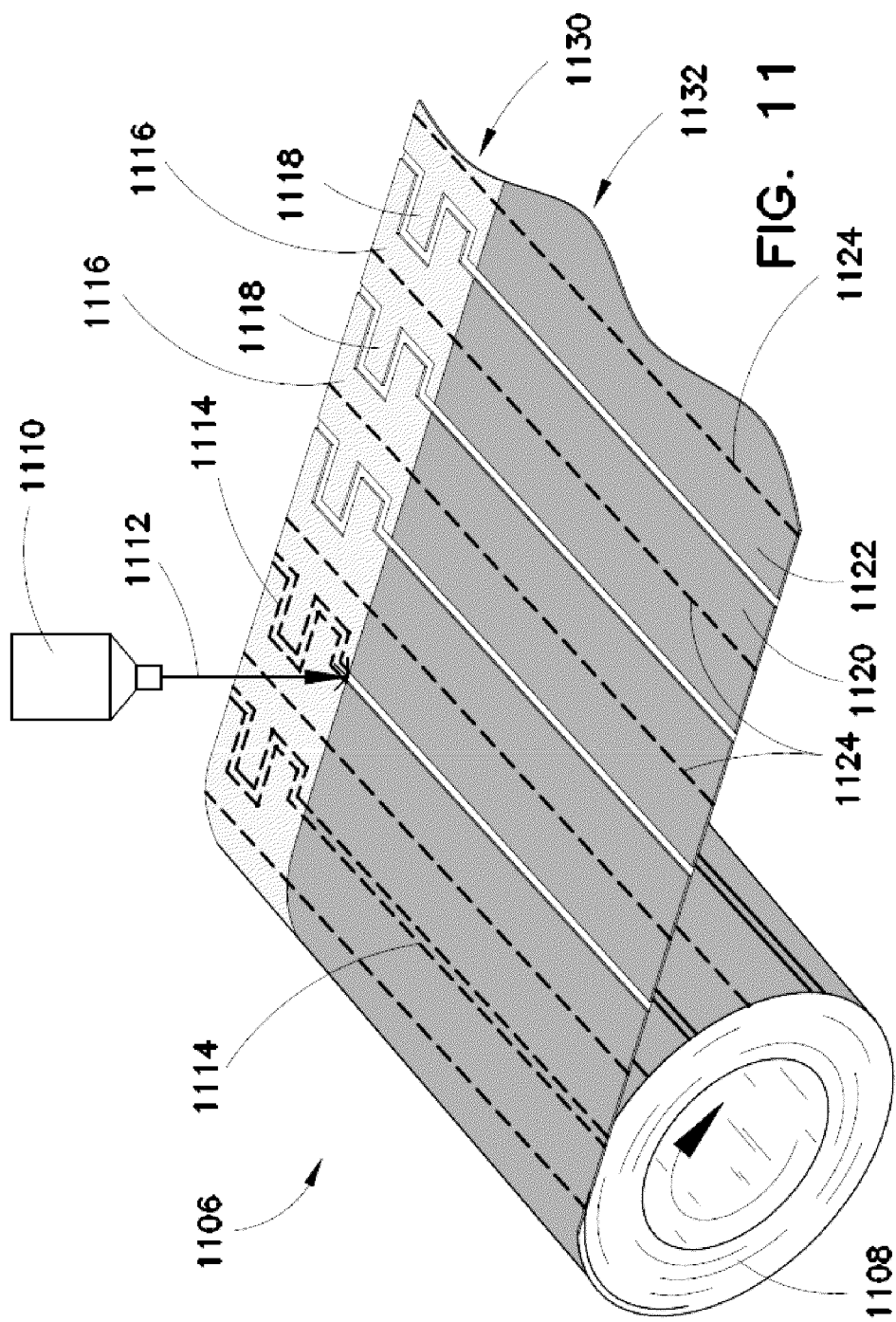
FIG. 11 is a perspective view showing a roll of base material having two conductive layers on it and a laser scribing technique being used to form electrical patterns.

FIG. 11 illustrates yet another of the simpler designs in which these teachings can be employed. In this embodiment, base material 1106 on roll 1108 is shown being unwound for forming a base substrate web comprising a plurality of rudimentary electrical patterns formed by laser scribing. In this embodiment, a laser apparatus 1110 projects a beam 1112 as apparatus 1110 is moved along the path indicated by dashed lines 1114. In so doing, multiple electrical patterns each comprising, e.g., counter electrode 1116, working electrode 1118, and traces 1120, 1122, are formed, the traces comprising electrical contacts at the ends opposite the electrodes. Separate base substrates to be assembled into individual biosensors, e.g., as described above, can be formed by cutting along dashed lines 1124. Instead of laser apparatus 1110, one of skill in the art would readily recognize other suitable means for removing the conductive material to form the electrical patterns, such as etching, mechanical removal of the conductive material and many others.

Figure 12:
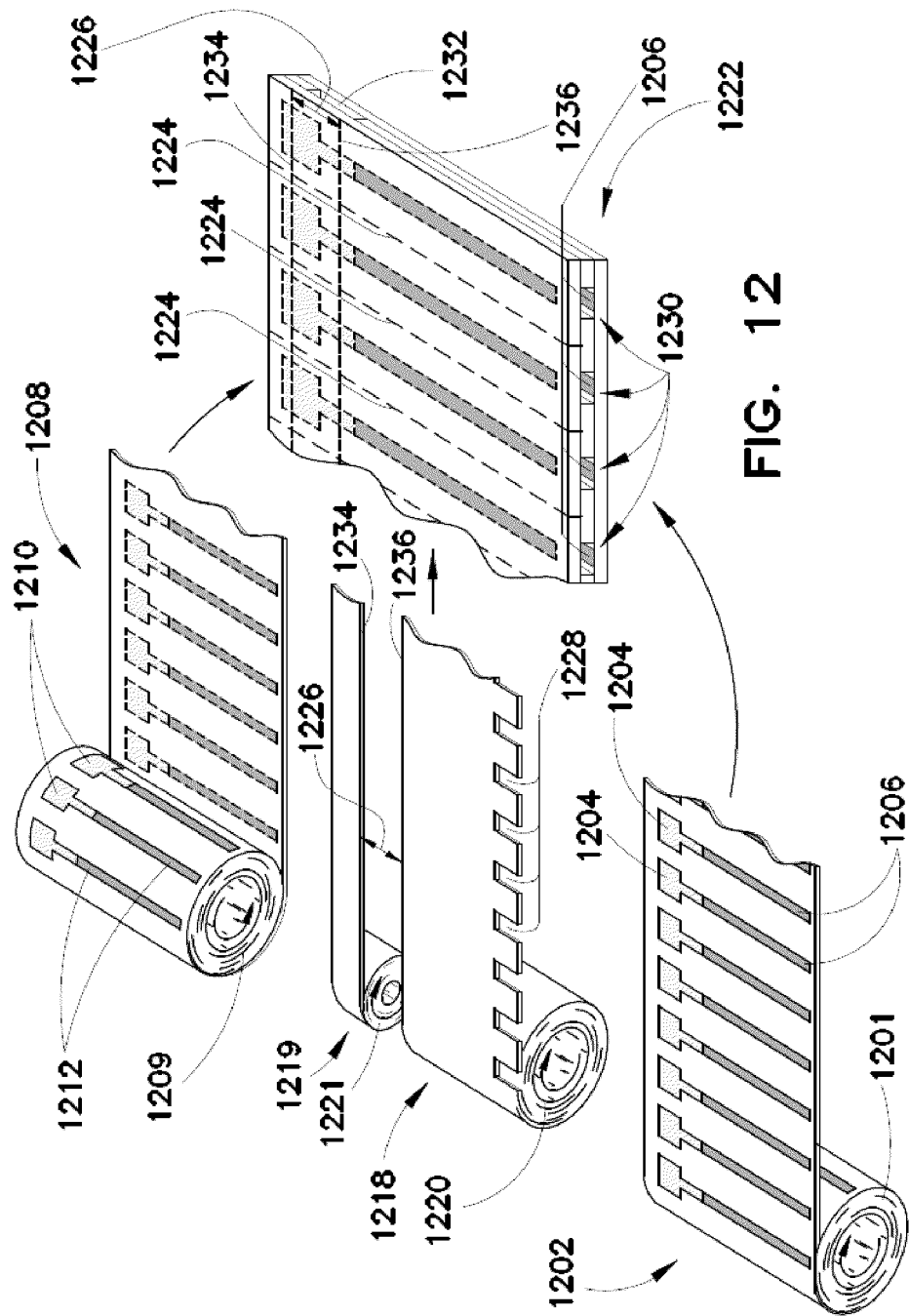
FIG. 12 is a perspective view schematically illustrating the production of an alternate biosensor embodiment employing these teachings.

One of skill in the art could also readily employ these teachings to form electrical patterns in multiple layers of a biosensor such as are found in biosensors having so-called "facing electrodes." For example, FIG. 12 shows a first roll 1201 of base substrate web 1202 having a series of working electrodes 1204 of one electrically conductive material and traces 1206 of a different electrically conductive material formed at spaced intervals thereon, which can be formed by the methods described herein. The ends of the traces comprise electrical contacts for meter insertion, as described elsewhere herein. Similarly, a second base substrate web 1208 is provided on roll 1209 and includes a series of counter electrodes 1210 made of one electrically conductive material and traces 1212 of a different electrically conductive material formed at spaced intervals thereon. Electrodes 1204 and 1210 can be formed of the same or different materials, as can traces 1206 and 1212.

In the embodiment illustrated in FIG. 12, two middle layers 1218 and 1219 of an electrically insulating material are provided on rolls 1220 and 1221, respectively. Rolls 1220 and 1221 are arranged during processing (unrolling) such that a gap 1226 that is defined between edges 1234 and 1236 is maintained. These middle layers form spacing layers in the biosensors produced and also define the capillary sample receiving chamber for the biosensors. Middle layer 1218 includes a plurality of rectangular notches 1228 formed in it that ultimately define openings 1230 in the biosensors produced to allow access by the electronics of a meter to electrical traces 1206 and 1212.

During production, the top and bottom webs 1208 and 1202, respectively, are laminated together and sandwich middle layers 1218 and 1219 therebetween to form the precursor or laminate structure 1222. Precursor 1222 includes a top layer formed from material 1208 having the counter electrodes 1210 formed on its underside, two side by side spaced middle insulating layers formed from material 1218 and 1219, and a bottom layer formed from material 1202 having the working electrodes 1204 formed on its top side. Examples of roll processing techniques that are used to form such a laminate structure can be found in U.S. Publication No. 2005/0016844, the disclosure of which was incorporated above by reference.

The precursor 1222 includes a series of openings 1230 that are defined by notches 1228 of layer 1218. The ends or contact portions of traces 1206 can be seen in the openings 1230 of laminate structure 1222. Edges 1234 and 1236 are shown in phantom in the precursor 1222, and gap 1226 forms a rectangular passageway 1232 with a series of working electrodes 1204 and counter electrodes 1210 spaced along its length and facing one another. The completed biosensors with "facing electrodes" are formed by cutting along dashed lines 1224. Each biosensor so formed will have sample receiving openings formed on both sides thereof and an access opening 1230, as is known in the art.

Of course, in some circumstances it may be desirable to form only one of the facing electrodes (or other electrical feature) from more than one electrically conductive material. For example, in the embodiment of FIG. 12, it may be desirable to form counter electrodes 1210 and traces 1212 of the same material. Generally, when these teachings are employed in facing electrode arrangements, at least one of the base substrate webs will have an electrical pattern with at least two regions of different electrically conductive material, and the two webs are combined into a laminate such as laminate 1222 with electrical patterns and/or electrical features arranged facing one another.

From the above teachings, one of skill in the art will appreciate that the electrical patterns and formation thereof described above can be employed in a wide variety of biosensor designs, ranging from biosensors having the most rudimentary electrical patterns, to those having highly sophisticated patterns providing multiple electrical functionalities, to those having electrical patterns or electrical features on multiple substrates, among others. Additionally, these teachings are not limited to depositing conductive layers on a base material and then removing portions of the conductive layers to form the electrical patterns.

Instead, electrical patterns having multiple regions could be directly deposited onto a base material to form a base substrate web without requiring further removal of conductive material from the base material to complete the electrical patterns. For example, in a technique such as "laser induced forward transfer" ("LIFT"), a pulsed laser beam is directed through a laser-transparent target substrate to strike a film of material coated on the opposite side of the target substrate. The laser vaporizes the film and, due to the transfer of momentum, the material is removed from the target substrate and is deposited on a receiving substrate that is placed in close proximity to the target substrate. This LIFT process obviously transpires quite rapidly, but it can be appreciated that the forming of the conductive material into the shape of the electrical patterns or portions thereof is at least initiated before transfer of the conductive material to the substrate is completed. Various methods for carrying out LIFT and similar techniques are disclosed in U.S. Pat. Nos. 6,177,151; 4,752,455; 5,725,706; 5,292,559; 5,492,861; 5,725,914; 5,736,464; 4,970,196 and 5,173,441, all of which are hereby incorporated herein by reference.

Figure 13:
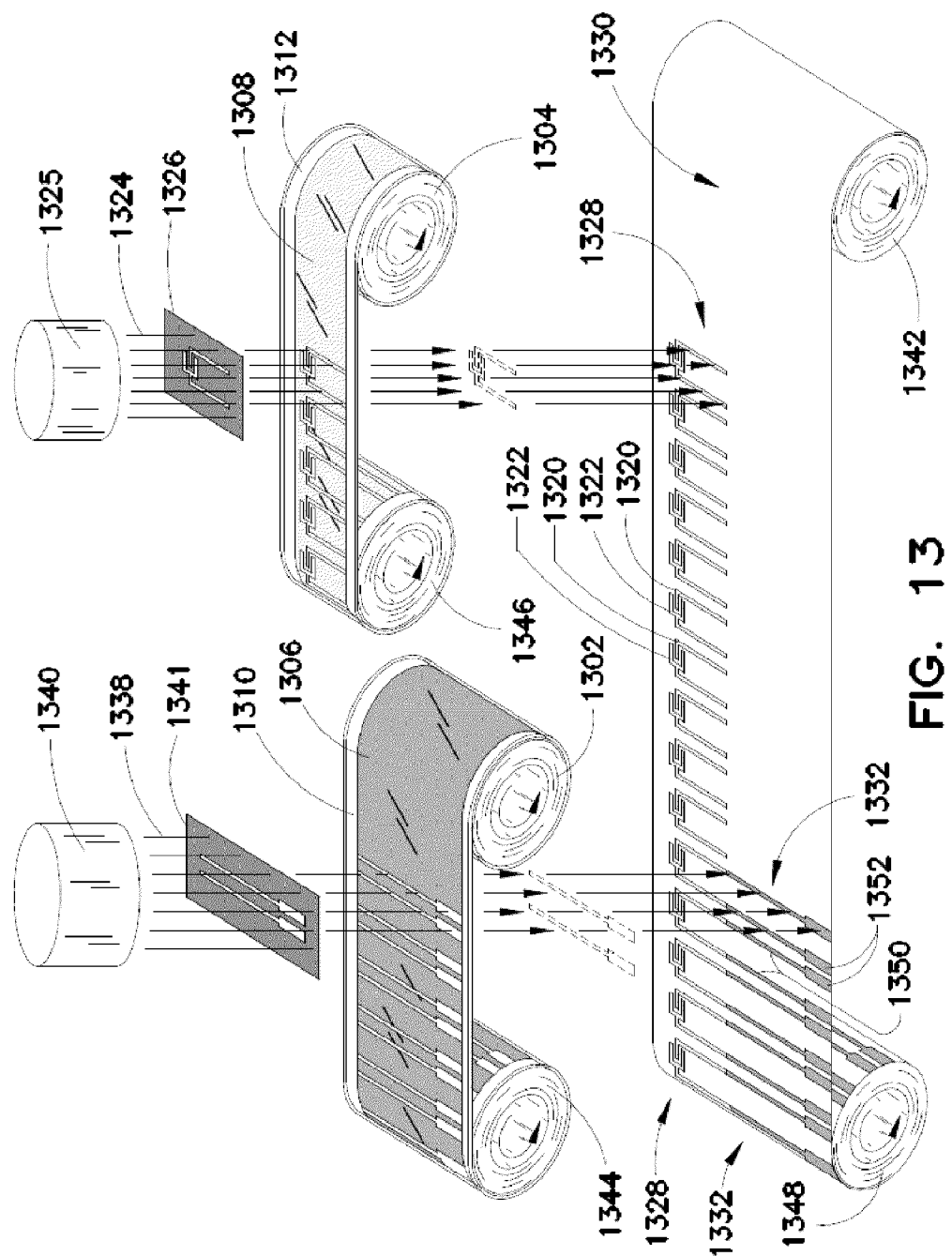
FIG. 13 is a perspective view schematically illustrating an alternate embodiment for producing electrical patterns useful for biosensors according to these teachings.

Turning to FIG. 13, two rolls 1302 and 1304 of different electrically conductive materials 1306 and 1308, respectively, are provided. Each roll has a top flexible layer 1310 and 1312, respectively, of laser transparent material to which the conductive materials 1306 and 1308 are adhered or otherwise coated or deposited, as described in the references incorporated above. Flexible laser-transparent layers 1310 and 1312 suitable for roll processing can be made from, e.g., polyethylene, polypropylene, polyvinyl acetate, polystyrene, polyethylene terephthalate, polybutylene terephthalate, and polytetrafluoroethylene, among others.

As illustrated in FIG. 13, the region 1328 of the electrical pattern that includes the working electrodes 1320 and counter electrodes 1322 is formed by projecting a broad field laser beam 1324 from laser apparatus 1325 through mask 1326, which results in first region 1328 of the electrical pattern being deposited on the base material 1330 as shown. Meanwhile, the same technique is used to form the second region 1332 of the electrical pattern downstream along base material 1330. That is, a broad field laser beam 1338 is projected from laser apparatus 1340 through mask 1341, which results in the second region 1332 of the electrical pattern having traces 1350 and contact pads 1352 being deposited on the base material 1330 as shown. Multiple electrical patterns are formed in this manner by coordinating the unwinding and indexing of rolls 1302, 1304 and 1342, which have take-up spools 1344, 1346 and 1348, respectively. The take-up spool 1348 of base material 1330 having electrical patterns thereon comprises the base substrate web that can be further processed to make biosensors through further roll processing and lamination techniques as described above.

As noted above, depending upon the particular conductive materials chosen for regions 1328 and 1332, it may be necessary to deposit a seed layer over region 1328 before depositing region 1332 of the electrical pattern. Such a seed layer in the form of a partial electrical pattern can be deposited by the same LIFT technique used to deposit regions 1328 and 1332. Similar to the layer approach described with reference to FIGS. 3-9, regions 1328 and 1332 can be formed spaced apart, and a connecting layer in the form of a partial pattern can be deposited therebetween. It may, e.g., be desirable to form the transition between the regions of the electrical pattern at a location where the pattern is least complicated, which may allow greater tolerances in the indexing and flexibility in the exact location at which the partial patterns must be deposited to sufficiently align.

While some laser direct write transfer techniques transfer a material from a laser transparent substrate, such is not necessary. For example, U.S. Pat. No. 4,895,735 to Cook ("the '735 patent") discloses a technique in which the conductive material is held above the substrate and a laser is used to deposit the conductive material in a pattern. Unlike the art discussed above, the conductive material is directly deposited without using a laser transparent substrate to which the conductive layer is adhered. These teachings can be used to incorporate such as process, as is illustrated with respect to FIG. 14.

Figure 14:
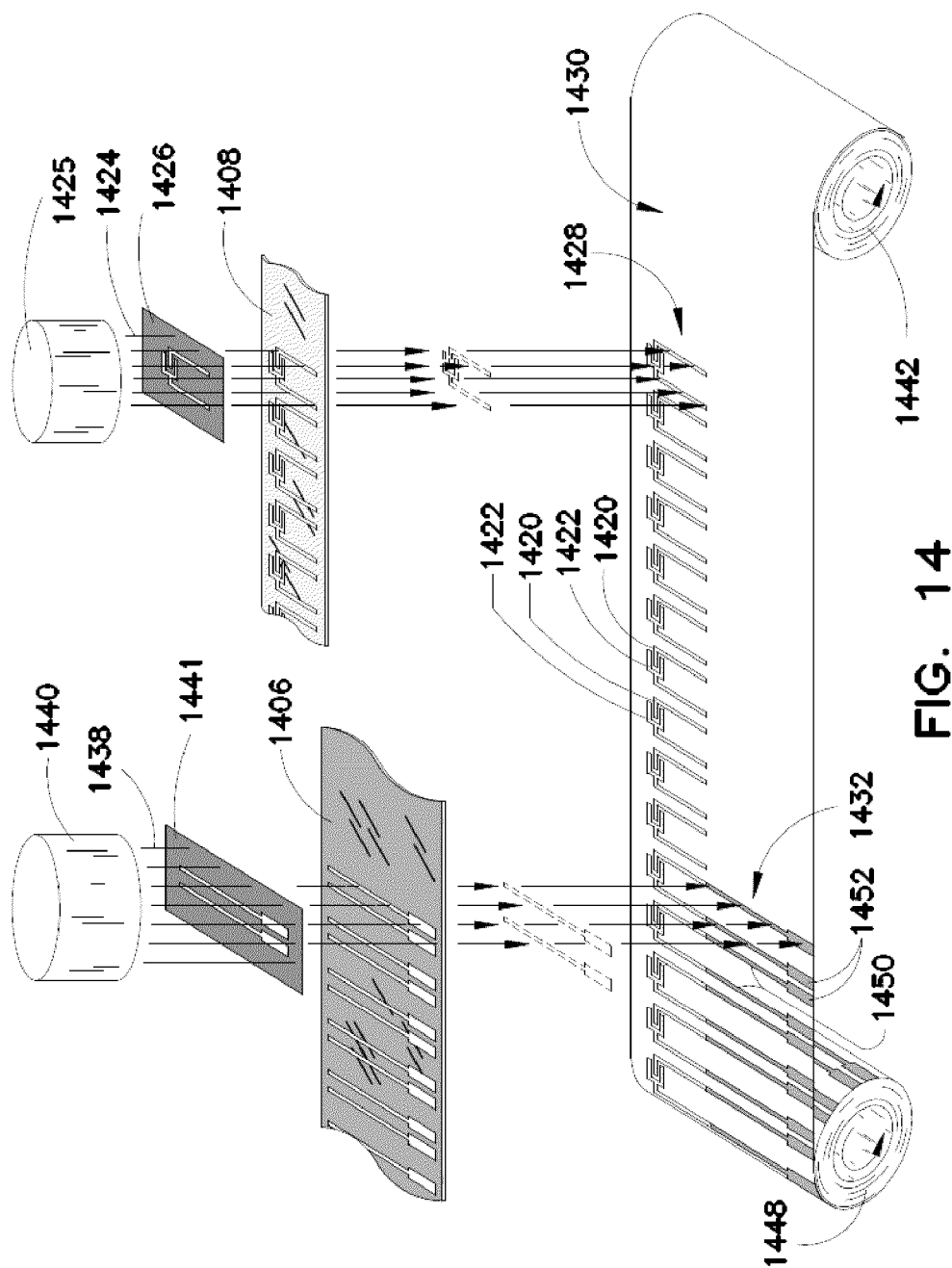
FIG. 14 is a perspective view schematically illustrating yet another alternate embodiment for producing electrical patterns useful for biosensors according to these teachings.

As shown in FIG. 14, two layers or films of different electrically conductive material 1406 and 1408 are placed directly above a base material 1430 that is provided in roll 1442. In order to minimize displacement of the layers 1406 and 1408, they may be fixed in place or laid on top of the base material 1430, as described in the '735 patent. As illustrated, the region 1428 of the electrical pattern that includes the working electrodes 1420 and counter electrodes 1422 is formed by projecting a broad field laser beam 1424 from laser apparatus 1425 through mask 1426, which results in first region 1428 of the electrical pattern being deposited on the base material 1430, as shown.

Meanwhile, the same technique of directly depositing a portion of the electrical pattern to the base material is used to form the second region 1432 of the electrical patterns downstream along material 1430. That is, a broad field laser beam 1438 is projected from laser apparatus 1440 through mask 1441, which results in the second region 1432 of the electrical pattern having traces 1450 and contact pads 1452 being deposited on the base material 1430 as shown. Multiple electrical patterns are formed in this manner by coordinating the unwinding and movement of the base material, the films, and/or laser apparatus, as desired. The take-up spool 1448 of base material 1430 having electrical patterns thereon comprises the base substrate web that can be further processed to make biosensors through further roll processing and lamination techniques as described above.

In addition to depositing the electrical pattern directly to the base material as was just described with reference to FIGS. 13 and 14, a broad laser pulse could be used to deposit an entire section or layer of material, thereby producing a base material having layers like those depicted in, e.g., FIGS. 3 and 6. Thereafter, laser ablation or other techniques described above can be used to remove a portion of the conductive materials to form the base substrate web having a plurality of electrical patterns each having multiple regions. One of skill in the art would readily recognize other variants for employing these teachings.

Regardless of the manner in which each conductive material layer is ultimately deposited on the base material, e.g., as a broad conductive layer or as a fully defined electrical feature, it will be appreciated from this disclosure that in an exemplary embodiment of the present invention, the first region typically comprises an electrode region having one or more electrically isolated electrodes, and the second region typically comprises a contact region comprising one or more electrically isolated contact areas, such as contact pads, wherein the electrode region and the contact region are electrically connected and are respectively comprised of the first and second different electrically conductive materials. As described above, the electrode region may be formed directly by a LIFT technique or by depositing the first electrically conductive material on the base material and removing at least a portion to define the desired electrical features for the electrode region. Similarly, the contact region may be formed directly by a LIFT technique or by depositing the second electrically conductive material on the base material and removing at least a portion to define the desired electrical features for the contact region. As also discussed above, the transition between the electrode and contact regions typically is located in the traces connecting these regions. In this case, each trace has one section formed of the first electrically conductive material connected to the electrode region and a second section formed of the second electrically conductive material connected to the contact region.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing a base substrate having an electrical pattern thereon for use in an electrochemical biosensor, the method comprising:
   providing a base material having a first layer of a first electrically conductive material positioned substantially side by side to and in electrical contact with a second layer of a second electrically conductive material, different from the first electrically conductive material; and
   then removing at least a portion of the first layer and the second layer to form an electrical pattern on the base material, the electrical pattern including a first region formed from the first electrically conductive material electrically connected to a second region formed from the second electrically conductive material, the first region of the electrical pattern comprising at least one electrode.

2. The method of claim 1, wherein the removing step comprises ablating the portion of the first layer and the second layer by projecting an image of the electrical pattern onto the base material with a laser apparatus to form the electrical pattern from both the first and second layers.

3. The method of claim 1, further comprising repeating the removing step a plurality of times at spaced intervals along the base material to form a base substrate web having a plurality of the electrical patterns thereon.

4. The method of claim 3, further comprising:
   depositing a reagent layer on the base substrate web over at least a portion of the at least one electrode of each electrical pattern of the plurality of electrical patterns;
   laminating at least one covering layer or a spacing layer over the base substrate web, thereby forming covers and sample receiving chambers for individual biosensors to be formed; and
   cutting through the at least one covering layer or spacing layer and the base substrate web to form a plurality of biosensors.

5. The method of claim 1, wherein the removing step comprises forming working and counter electrodes from the first electrically conductive material and forming contact pads from the second electrically conductive material.

6. The method of claim 1, wherein the providing step comprises providing the base material with the first layer formed from a noble metal and the second layer formed from an electrically conductive material substantially more robust than a noble metal.

7. The method of claim 6, wherein the noble metal is selected from the group consisting of gold, silver, palladium and platinum.

8. The method of claim 6, wherein the electrically conductive material for the second layer is selected from the group consisting of aluminum, carbon, cobalt, copper, gallium, indium, iridium, iron, lead, magnesium, mercury, nickel, niobium, osmium, rhenium, rhodium, selenium, silicon, tantalum, tin, titanium, tungsten, uranium, vanadium, zinc, zirconium, indium tin oxide and mixtures thereof.

9. The method of claim 1, wherein the providing step comprises providing the base material with the first and second layers in a partially overlapping arrangement.

10. The method of claim 1, further comprising, prior to the providing step, depositing the first and second layers of electrically conductive material substantially side by side along a portion of the base material.

11. The method of claim 10, further comprising:
    prior to the providing step, depositing third and fourth layers of electrically conductive material substantially side by side along a second portion of the base material, the third layer being adjacent to the second electrically conductive layer; and
    cutting the base material between the second and third layers.

12. The method of claim 10, wherein the depositing step comprises one or more of sputtering, physical vapor deposition, plasma assisted chemical vapor deposition, chemical vapor deposition, electron beam physical vapor deposition, metal-organic chemical vapor deposition, and laser induced forward transfer.

13. The method of claim 1, further comprising providing a second base material having a second electrical pattern formed thereon and combining the first base material and the second base material into a laminate in which the first electrical pattern faces the second electrical pattern.

14. A method of manufacturing a base substrate web comprising a plurality of electrical patterns for use in electrochemical biosensors, the method comprising:
    providing an electrically insulating base material;
    depositing first and second different electrically conductive materials on a portion of the base material substantially side by side to one another; and
    forming a plurality of electrical patterns on the portion of the base material, each electrical pattern including a first region formed from the first electrically conductive material electrically connected to a second region formed from the second electrically conductive material, the first region of the electrical pattern comprising at least a pair of electrodes formed from the first electrically conductive material, the pair of electrodes including a working electrode.

15. The method of claim 14, wherein the depositing step comprises depositing a first layer of the first electrically conductive material on the portion of the base material and depositing a second layer of the second electrically conductive material on the portion of the base material substantially side by side to and in electrical contact with the first layer, further wherein the step of forming the electrical patterns comprises removing a portion of the first layer and the second layer after the depositing step.

16. The method of claim 15, wherein the removing step comprises forming working and counter electrodes from the first electrically conductive material and forming contact pads from the second electrically conductive material.

17. The method of claim 14, wherein the depositing step comprises depositing a noble metal as the first electrically conductive material and depositing a material that is substantially more robust than a noble metal as the second electrically conductive material.

18. The method of claim 17, wherein the noble metal is selected from the group consisting of gold, silver, palladium and platinum.

19. The method of claim 17, wherein the second electrically conductive material is selected from the group consisting of aluminum, carbon, cobalt, copper, gallium, indium, iridium, iron, lead, magnesium, mercury, nickel, niobium, osmium, rhenium, rhodium, selenium, silicon, tantalum, tin, titanium, tungsten, uranium, vanadium, zinc, zirconium, indium tin oxide and mixtures thereof.

20. The method of claim 14, wherein at least one of the first and second electrically conductive materials substantially comprises the shape of a portion of the electrical pattern before the depositing step is complete.

21. The method of claim 20, wherein the depositing step comprises laser induced forward transfer.

22. The method of claim 14, further comprising depositing third and fourth different electrically conductive materials substantially side by side along a second portion of the base material and cutting the base material to separate the portion from the second portion.

23. The method of claim 22, further comprising:
forming a plurality of second electrical patterns on the second portion of the base material;
incorporating the portion of base material having the first and second electrically conductive materials into a first set of biosensors; and
incorporating the second portion of the base material having the third and fourth electrically conductive materials into a second set of biosensors.

24. The method of claim 23, wherein the first and second electrically conductive materials are the same as the third and fourth electrically conductive materials, respectively, whereby the first and second sets of biosensors are the same.

25. The method of claim 14, further comprising:
depositing a reagent layer on the base substrate web over at least a portion of the at least one electrical feature of each electrical pattern of the plurality of electrical patterns;
laminating at least one covering layer or a spacing layer over the base material, thereby forming covers and sample receiving chambers for individual biosensors to be formed; and
cutting through the at least one covering layer or spacing layer and the base substrate web to form a plurality of biosensors.

26. The method of claim 14, further comprising:
providing a second base material having a plurality of second electrical patterns formed thereon; and
combining the first base material and the second base material into a laminate in which each electrical pattern of the plurality of electrical patterns faces a respective second electrical pattern of the plurality of second electrical patterns.

27. A method for manufacturing a base substrate having an electrical pattern thereon for use in an electrochemical biosensor, comprising the steps of:
providing an electrically insulating base material;
forming an electrode region on the base material, the electrode region comprising at least a pair of electrically isolated electrodes formed of a first electrically conductive material, the pair of electrodes including a working electrode;
forming a contact region on the base material adjacent the electrode region, the contact region comprising at least first and second electrically isolated contact areas formed of a second electrically conductive material, the first and second electrically conductive materials being different; and
forming at least first and second electrically isolated traces on the base material, each trace having a first section and a second section, the first section being formed from the first electrically conductive material and being electrically connected to the electrode region, the second section being formed from the second electrically conductive material and being electrically connected to the contact region;
wherein the first and second contact areas are each in electrical contact with a corresponding one of the pair of electrodes through a corresponding one of the traces, further wherein the electrode region, the traces and the contact region cooperate to define an electrical pattern for the biosensor.

28. The method of claim 27, further comprising:
providing the base material with a first layer formed of the first electrically conductive material positioned substantially side by side to and in electrical contact with a second layer formed of the second electrically conductive material; and
removing at least a portion of the first layer and the second layer to form the electrical pattern on the base material.

29. The method of claim 28, wherein the removing step comprises ablating the portion of the first layer and the second layer by projecting an image of the electrical pattern onto the base material with a laser apparatus to form the electrical pattern from both the first and second layers.

30. The method of claim 29, further comprising repeating the removing step a plurality of times at spaced intervals along the base material to form a base substrate web having a plurality of the electrical patterns thereon.

31. The method of claim 30, further comprising:
depositing a reagent layer on the base substrate web over at least a portion of the at least one electrode of each electrical pattern of the plurality of electrical patterns;
laminating at least one covering layer or a spacing layer over the base substrate, thereby forming covers and sample receiving chambers for individual biosensors to be formed; and
cutting through the at least one covering layer or spacing layer and the base substrate web to form a plurality of biosensors.

32. The method of claim 28, wherein the providing step comprises providing the base material with the first and second layers in a partially overlapping arrangement.

33. The method of claim 28, further comprising, prior to providing the base material, depositing the first and second layers of electrically conductive material substantially side by side along a portion of the base material.

34. The method of claim 33, wherein the depositing step comprises one or more of sputtering, physical vapor deposition, plasma assisted chemical vapor deposition, chemical vapor deposition, electron beam physical vapor deposition, metal-organic chemical vapor deposition, and laser induced forward transfer.

35. The method of claim 27, wherein the first electrically conductive material comprises a noble metal and the second electrically conductive material comprises a material substantially more robust than a noble metal.

36. The method of claim 35, wherein the noble metal is selected from the group consisting of gold, silver, palladium and platinum.

37. The method of claim 35, wherein the second electrically conductive material is selected from the group consisting of aluminum, carbon, cobalt, copper, gallium, indium, iridium, iron, lead, magnesium, mercury, nickel, niobium, osmium, rhenium, rhodium, selenium, silicon, tantalum, tin, titanium, tungsten, uranium, vanadium, zinc, zirconium, indium tin oxide and mixtures thereof.

38. The method of claim 27, further comprising providing a second base material having a second electrical pattern formed thereon and combining the first base material and the second base material into a laminate in which the first electrical pattern faces the second electrical pattern.

39. The method of claim 27, wherein at least a portion of the electrode region, contact region or the traces is formed by laser induced direct transfer.

40. The method of claim 1, wherein the first region includes a dosing end of a biosensor from which the substrate is formed and the second region includes a meter insertion end of the biosensor.

41. The method of claim 1, wherein the second region comprises a contact pad.

42. The method of claim 1, wherein the first and second regions are disposed on opposite ends of the base substrate.

* * * * *